US010851126B2

(12) United States Patent
Hogkinson et al.

(10) Patent No.: US 10,851,126 B2
(45) Date of Patent: Dec. 1, 2020

(54) COMPLEXES AND METHODS FOR THEIR PREPARATION

(71) Applicant: JOHNSON MATTHEY PUBLIC LIMITED COMPANY, London (GB)

(72) Inventors: Roy Hogkinson, West Midlands (GB); Vaclav Jurcik, Hertfordshire (GB); Hans Guenter Nedden, Hertfordshire (GB); Martin Wills, West Midlands (GB)

(73) Assignee: Johnson Matthey Public Limited Company, London (GB)

( * ) Notice: Subject to any disclaimer, the term of this patent is extended or adjusted under 35 U.S.C. 154(b) by 110 days.

(21) Appl. No.: 15/512,347

(22) PCT Filed: Sep. 11, 2015

(86) PCT No.: PCT/GB2015/052632
§ 371 (c)(1),
(2) Date: Mar. 17, 2017

(87) PCT Pub. No.: WO2016/042298
PCT Pub. Date: Mar. 24, 2016

(65) Prior Publication Data
US 2017/0275317 A1 Sep. 28, 2017

(30) Foreign Application Priority Data

Sep. 19, 2014 (GB) .................................. 1416628.4

(51) Int. Cl.
*C07C 303/38* (2006.01)
*C07F 15/00* (2006.01)
*C07C 303/40* (2006.01)
*C07C 311/18* (2006.01)
*B01J 31/18* (2006.01)
*C07B 35/02* (2006.01)
*C07C 311/17* (2006.01)

(52) U.S. Cl.
CPC ....... *C07F 15/0046* (2013.01); *B01J 31/1805* (2013.01); *C07B 35/02* (2013.01); *C07C 303/38* (2013.01); *C07C 303/40* (2013.01); *C07C 311/17* (2013.01); *C07C 311/18* (2013.01); *B01J 2231/64* (2013.01); *B01J 2531/821* (2013.01); *C07C 2601/16* (2017.05)

(58) Field of Classification Search
None
See application file for complete search history.

(56) References Cited

U.S. PATENT DOCUMENTS

2004/0229870 A1* 11/2004 Horvath ............... C07D 213/73
514/229.5

FOREIGN PATENT DOCUMENTS

| WO | WO2006017215 A2 | 2/2006 |
| WO | WO 2007147897 A1 | 12/2007 |
| WO | WO2010106364 A2 | 9/2010 |
| WO | WO 2011026682 A1 | 3/2011 |
| WO | WO2012026201 A1 | 3/2012 |
| WO | WO2012147944 A1 | 11/2012 |
| WO | WO2014068331 A1 | 5/2014 |

OTHER PUBLICATIONS

Micovic et al., Communication from the Institute of Chemistry of the Serbian Academy of Sciences and the Institute of Chemistry of the Faculty of Sciences in Belgrade, 1953, 1190.*
Ravinder et al.,Tetrahedron Letters, 2013, (54), 4908.*
Martins et al. (Tetrahedron: Assymetry, 2008, 19(10), 1250).*
Bon et al. (J. Org. Chem., 1994, 59(7), 1904).*
Alazard et al. (Tetrahedron, 1990, 46(5), 1578).*
STN abstract of Alazard et al. (Tetrahedron, 1990, 46(5), 1578).*
GB1516107.8, UK Combined Search and Examination Report under Sections 17 and 18(3), dated Jun. 16, 2016.
GB1416628.4 Search Report under Section 17(5) dated Jul. 8, 2015.
PCT/GB2015/052632, International Search Rpoert and Written Opinion dated Dec. 10, 2015.
Bream et al., "Synthesis of 1- and 5-Aryl-2, 4-benzothiazepines. 25th Communication on Seven-membered Heterocycles," Helvitica Chimica Acta, vol. 60, No. 8, Dec. 14, 1977, 2872-2880.
Chandrakumar et al., "Preparation and Opioid Activity of Analogues of the Analgesic Dipeptide 2,6-Dimethyl-L-Tyrosyl-N-(3-Phenylpropyl)-D-Alaninamide," Journal of Medicinal Chemistry, vol. 35, No. 2, Jan. 1, 1992, 223-233.
Ishihara et al., "Design of an Organocatalyst for the Enantioselective Diels-Alder Reaction With α-Acyloxyacroleins," Journal of the American Chemical Society, vol. 127, No. 30, Aug. 1, 2005, 10504-10505.
Ishihara et al., "Design of an Organocatalyst for the Enantioselective Diels-Alder Reaction With α-Acyloxyacroleins," Journal of the American Chemical Society, Aug. 3, 2005, S1-S17.
Miyazaki et al., "Synthesis and Evaluation of 4-Substituted Benzylamine Derivatives as Beta-Tryptase Inhibitors," Bioorganic & Medicinal Chemistry Letters, vol. 16, No. 11, Jun. 1, 2006, 2986-2990.
Garrity et al., "A New Synthetic Route to 2-(P-Nitrobenzyl)-1,4,7,10-Tetraazacyclododecane," Tetrahedron Letters, vol. 34, No. 35, Jan. 1, 1993, 5531-5534.
Stoll et al., "Eine neue Synthese von Bufotenin und verwandten Oxy-tryptaminen. 40. Mitteilung uber Mutterkornalkaloide," Helvetica Chimica Acta, vol. 38, No. 6, Jan. 1, 1955, 1452-1472.
ChemFiles, Peptide Synthesis, ALDRICH, vol. 7, No. 2, 2007, 1-20.
Fujimoto et al., "Synthesis, Opioid Receptor Binding Profile, and Antinociceptive Activity of 1-Azaspiro[4.5]decan-10-yl Amides," Journal of Medicinal Chemistry, vol. 32, No. 6, 1989, 1259-1265.
Hayes et al., "A Class of Ruthenium(II) Catalyst for Asymmetric Transfer Hydrogenations of Ketones," Journal of American Chemical Society, vol. 127, 2005, 7318-7319.
Jolley et al., "Application of Tethered Ruthenium Catalysts to Asymmetric Hydrogenation of Ketones, and the Selective Hydrogenation of Aldehydes," Adv. Synth. Catal., 2012, vol. 354, 2545-2555.
Martins et al., "Asymmetric Hydrogenation of Ketones Using Ir(III) Complexes of N-alkyl-N'-tosyl-1,2-ethanediamine Ligands," Tetrahedron Letters, vol. 50, 2009, 688-692.

(Continued)

*Primary Examiner* — Sudhakar Katakam
*Assistant Examiner* — Jennifer C Sawyer
(74) *Attorney, Agent, or Firm* — BakerHostetler

(57) ABSTRACT

Disclosed are methods for the preparation of ligands for complexes, methods for preparing complexes and complexes having those ligands. Also provided is the use of a complex as a catalyst in a method of synthesis.

18 Claims, No Drawings

(56) References Cited

OTHER PUBLICATIONS

Soni et al., "Director Formation of Tethered Ru(II) Catalysts Using Arene Exchange," Organic Letters, 2013, vol. 15, No. 19, 5110-5113.
Stodt et al., "Preparation, Reactivity and Peptide Labelling Properties of (η6-Arene)ruthenium(11) Complexes With Pendant Carboxylate Groups," Eur. J. Inorg. Chem., 2003, 1873-1882.
Tan et al., "pH-Regulated Transfer Hydrogenation of Quinoxalines With a Cp*Ir-diamine Catalyst in Aqueous Media," Tetrahedron, vol. 67, 2011, 6206-6213.
H.C. Brown, Sixty Years of Hydride Reductions, Reductions in Organic Synthesis, Abdel-Magid, A.; ACS Symposium Series, American Chemical Society, Washington, D.C., 1996.
J.C. Fettinger, Hydroalumination of Alkenes and Alkynes by Primary Aluminum Hydrides Under Mild Conditions, Organometallics 2014, 33, 6232-6240.
E.H. Gold et al., Reductive Cleavage of Sulfonamides With Sodium Bis(2-methoxyethoxy)aluminum Hydride, Journal of Organic Chemistry, vol. 37, No. 13, 1972, 2208-2210.
W.Paterson et al., The Removal of Toluene-p-sulphonyl Groups From Sulphonamides, Part I. Synthesis of Schiff Bases, Journal of the Chemical Society, 1965, 485-489.
B.Thiedemann, Reduction of N-Allylamides by LiAlH4: Unexpected Attack of the Double Bond with Mechanistic Studies of Product and Byproduct Formation, The Journal of Organic Chemistry, 2014, 79, 10284-10295.

* cited by examiner

COMPLEXES AND METHODS FOR THEIR PREPARATION

FIELD OF THE INVENTION

This invention relates to methods for the preparation of ligands for complexes, methods for preparing complexes and complexes having those ligands. Also provided is the use of a complex as a catalyst in a method of synthesis.

BACKGROUND

Recent developments in asymmetric transfer hydrogenation have seen the introduction of highly stable and highly active ruthenium (II) (Ru(II)) catalysts. Work in this area has shown that catalytic activity may be improved when a diamine and a $\eta^6$ aryl group are contained within a single ligand with these functional groups connected by a tether. An example catalyst of this type is disclosed by Hayes et al. (*J. Am. Chem. Soc.* 2005, 127, 7318), and is shown below.

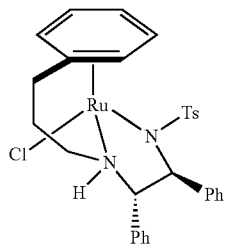

Hayes et al. describe the preparation of ruthenium (II) catalysts for use in asymmetric transfer hydrogenation reactions. The catalysts are prepared from a diene-containing diamino compound 5, which is reacted with ruthenium trichloride to yield an intermediate dimer species 6. This dimer is converted to the catalyst product (shown above) using an organic base.

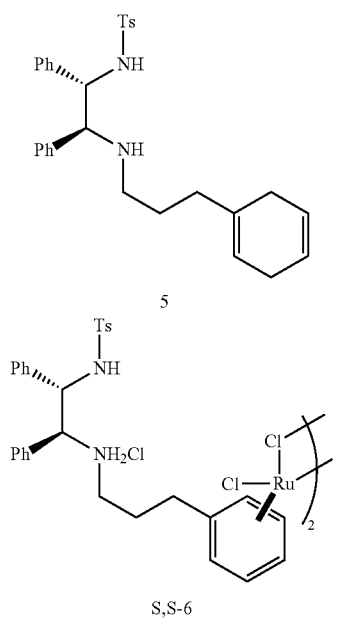

The compound 5 is a precursor which is generated by reductive amination of an appropriate aldehyde with TsDPEN. The yield for the two step reductive amination process is 47%. It is noted that the aldehyde must also be prepared in a separate step, typically from the corresponding alcohol, and this adds to the cost and complexity of preparing the ligand precursor on a large scale.

The present applicant has previously described the preparation of a hydrogenation catalyst in WO 2010/106364. It is noted in WO 2010/106364 that the reductive amination approach results in the formation of a contaminating by-product. This is said to complicate the subsequent purification of the ligand precursor. WO 2010/106364 describes the reductive amination as problematic and therefore provides an improved alkylation method for preparing a ligand precursor.

In the method of Hayes et al. the aldehyde for the reductive amination is prepared from a corresponding alcohol, for example using Swern oxidation conditions. As an alternative WO 2010/106364 describes the activation of the alcohol as a sulfonate. This sulfonate-containing compound is then reacted with an amino-containing compound, such as TsDPEN, to generate the ligand precursor.

WO 2014/068331 describes a ligand swapping method for the preparation of tethered complexes. The ligands used are prepared using an alkylation method.

Similarly, WO 2012/026201 describes ruthenium-diamine complexes having an oxygen or sulfur atom in the tether. It is described that the ligands are prepared using an alkylation approach.

The alcohol activation approach is not without problems. The product from the reaction between the activated alcohol and the amino-containing compound is itself capable of reacting with the activated alcohol, which leads to the generation of undesirable by-products.

The present inventors have recognised that the known preparations of ligands are problematic and there is a need to improve these methods in order to generate ligands and complexes in good yield and in high purity. The present invention provides improved methods for synthesising ligands and complexes. The methods described herein provide greater selectivity during the preparation of a ligand for a metal complex, which may find use as a metal catalyst.

SUMMARY OF THE INVENTION

In a general aspect the present invention provides improved methods for the preparation of ligands, where such ligands find use in the preparation of metal complexes such as metal catalysts. The ligands may be provided in high yield and with few impurities. The methods of the invention avoid the need to use an aldehyde intermediate.

The present inventors have found that a ligand of formula (I) may be prepared via an amide intermediate (II). Thus, in a first aspect of the invention there is provided a method of preparing an amine compound of formula (I), the method comprising the steps of:
  (i) preparing an amide of formula (II); and
  (ii) reacting the amide of formula (II) to form the amine compound of formula (I),
and (I) and (II) have the structures shown below:

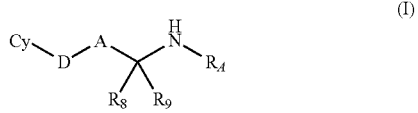

-continued

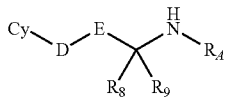

(II)

and Cy, D, A, $R_8$, $R_9$, $R_A$ and E are as defined below.

$R_A$ is —$SO_2R_{10}$ or —$R_N$, where $R_{10}$ is an optionally substituted straight, branched or cyclic $C_{1-10}$ alkyl, an optionally substituted $C_{6-10}$ aryl or —$NR_{11}R_{12}$, where $R_{11}$ and $R_{12}$ are independently selected from the group consisting of optionally substituted straight- or branched-chain $C_{1-10}$ alkyl and optionally substituted $C_{6-10}$ aryl, and $R_N$ is hydrogen, or straight, branched or cyclic $C_{1-10}$ alkyl;

Cy is optionally substituted $C_{6-20}$ aryl or optionally substituted $C_{5-6}$ cycloalkadienyl;

D is an optionally substituted straight- or branched-chain $C_{1-4}$ alkyl group, or D is a group:

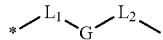

where $L_1$ is a covalent bond or optionally substituted $C_{1-3}$ alkyl; and $L_2$ is a covalent bond or optionally substituted $C_{1-2}$ alkyl;

G is selected from —O—, —S—, and optionally substituted $C_{6-10}$ aryl, optionally substituted $C_{3-10}$ heteroaryl and optionally substituted $C_{6-10}$ cycloalkyl;

and the asterisk indicates the point of attachment to Cy;

A is *—$CH_2NHC(R_6R_7)$— or *—$C(R_4R_5)NHCH_2$—, where the asterisk indicates the point of attachment to D;

E is *—$C(O)NHC(R_6R_7)$— or *—$C(R_4R_5)NHC(O)$—, where the asterisk indicates the point of attachment to D;

$R_4$ and $R_5$ are each independently selected from the group consisting of hydrogen, straight- or branched-chain $C_{1-20}$ alkyl, straight, branched or cyclic $C_{1-10}$ alkoxy, $C_{6-10}$ aryl and $C_{6-10}$ aryloxy, —OH, —CN, and —$CF_3$;

$R_6$, $R_7$, $R_8$ and $R_9$ are each independently selected from the group consisting of hydrogen, optionally substituted straight, branched or cyclic $C_{1-20}$ alkyl, optionally substituted straight, branched or cyclic $C_{1-20}$ alkoxy, optionally substituted $C_{6-20}$ aryl and optionally substituted $C_{6-20}$ aryloxy, or $R_6$ and $R_7$ together with the carbon atom to which they are bound and/or $R_8$ and $R_9$ together with the carbon atom to which they are bound form an optionally substituted $C_{3-20}$ cycloalkyl or an optionally substituted $C_{2-20}$ cycloalkoxy, or one of $R_6$ and $R_7$ and one of $R_8$ and $R_9$ together form an optionally substituted $C_{5-10}$ cycloalkyl or an optionally substituted $C_{5-10}$ cycloalkoxy.

The optional substituents are described in further detail below.

In another aspect of the invention there is provided a method of preparing an amine compound of formula (I), the method comprising the step of:

(ii) reacting an amide of formula (II) to form the amine compound of formula (I), and (I) and (II) have the structures shown below:

(I)

-continued

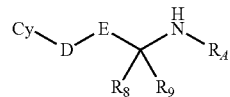

(II)

and Cy, D, A, $R_8$, $R_9$, $R_A$ and E are as defined below.

$R_A$ is —$SO_2R_{10}$ or —$R_N$, where $R_{10}$ is an optionally substituted straight, branched or cyclic $C_{1-10}$ alkyl, an optionally substituted $C_{6-10}$ aryl or —$NR_{11}R_{12}$, where $R_{11}$ and $R_{12}$ are independently selected from the group consisting of optionally substituted straight- or branched-chain $C_{1-10}$ alkyl and optionally substituted $C_{6-10}$ aryl, and $R_N$ is hydrogen, or straight, branched or cyclic $C_{1-10}$ alkyl;

Cy is optionally substituted $C_{6-20}$ aryl or optionally substituted $C_{5-6}$ cycloalkadienyl;

D is an optionally substituted straight- or branched-chain $C_{1-4}$ alkyl group, or D is a group:

where $L_1$ is a covalent bond or optionally substituted $C_{1-3}$ alkyl; and $L_2$ is a covalent bond or optionally substituted $C_{1-2}$ alkyl;

G is selected from —O—, —S—, and optionally substituted $C_{6-10}$ aryl, optionally substituted $C_{3-10}$ heteroaryl and optionally substituted $C_{6-10}$ cycloalkyl;

and the asterisk indicates the point of attachment to Cy;

A is *—$CH_2NHC(R_6R_7)$— or *—$C(R_4R_5)NHCH_2$—, where the asterisk indicates the point of attachment to D;

E is *—$C(O)NHC(R_6R_7)$— or *—$C(R_4R_5)NHC(O)$—, where the asterisk indicates the point of attachment to D;

$R_4$ and $R_5$ are each independently selected from the group consisting of hydrogen, straight- or branched-chain $C_{1-20}$ alkyl, straight, branched or cyclic $C_{1-10}$ alkoxy, $C_{6-10}$ aryl and $C_{6-10}$ aryloxy, —OH, —CN, and —$CF_3$;

$R_6$, $R_7$, $R_8$ and $R_9$ are each independently selected from the group consisting of hydrogen, optionally substituted straight, branched or cyclic $C_{1-20}$ alkyl, optionally substituted straight, branched or cyclic $C_{1-20}$ alkoxy, optionally substituted $C_{6-20}$ aryl and optionally substituted $C_{6-20}$ aryloxy, or $R_6$ and $R_7$ together with the carbon atom to which they are bound and/or $R_8$ and $R_9$ together with the carbon atom to which they are bound form an optionally substituted $C_{3-20}$ cycloalkyl or an optionally substituted $C_{2-20}$ cycloalkoxy, or one of $R_6$ and $R_7$ and one of $R_8$ and $R_9$ together form an optionally substituted $C_{5-10}$ cycloalkyl or an optionally substituted $C_{5-10}$ cycloalkoxy.

The optional substituents are described in further detail below.

In one embodiment, the method may comprise a first step of:

(i) preparing the amide of formula (II).

In one embodiment, the amine compound (I) is a compound (Ia):

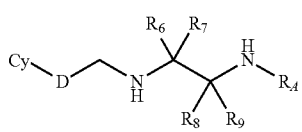

For example, compound (Ia) may be a compound of formula (Ic):

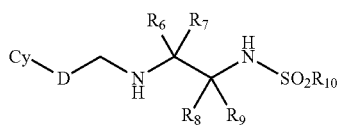

In one embodiment, the amine compound (I) is a compound (Ib):

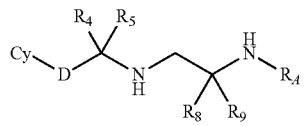

For example, compound (Ia) may be a compound of formula (Id):

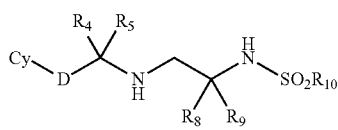

In one embodiment, step (i) comprises the preparation of the amide of formula (II) from an amine of formula (III) and a carboxylic acid of formula (IV). The carboxylic acid may be an activated carboxylic acid, such as an acid chloride or an activated ester. The activated carboxylic acid may be generated in situ from the carboxylic acid. Amide (III) and carboxylic (IV) are as defined below.

In one embodiment, step (ii) comprises the reduction of the amide of formula (II), for example with a reducing agent, such as a metal hydride. Alternatively, the amide may be reduced in the presence of a metal catalyst, for example in the presence of hydrogen.

The inventors have found that the amide formation and reduction steps provide the compound of formula (I) in high yield and with minimal impurities. This provides an advantage over known methods for the preparation of the compounds of formula (I), where there are contaminating by-products. An additional advantage is that an amide (II) may be more readily and easily purified on account of the fact that is relatively easy to separate the desired amide from the other components of the reaction, such as amine by-products. It follows that the amine (I) may be produced with high purity as it is derived from a high purity starting material.

The inventors have found that the use of a reducing agent is tolerated by other functionality present in the amide compound of formula (II) and the product (I). For example, the inventors have found that the diene functionality in amide (II) and amine (I), where present, is not reduced during the reaction, even when a strong reducing agent such as $LiAlH_4$ is used.

The ligands of formula (I), obtained according to the methods of the first and second aspects of the invention, may be used to prepare a complex of formula (X). In a third aspect of the invention there is provided a method for preparing a complex of formula (X), the method comprising the steps of:

(i) preparing an amide of formula (II);
(ii) reacting the amide of formula (II) to form the amine compound of formula (I); and
(iii) reacting the amine compound of formula (I), optionally as an acid addition salt, with a transition metal compound, to form a complex of formula (X),
where the complex of formula (X) has the structure shown below:

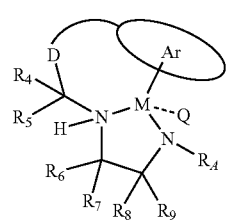

where D, $R_4$, $R_5$, $R_6$, $R_7$, $R_8$, and $R_9$, are as defined above for the compounds of formula (I), (Ia) and (Ib), and $R_A$ is $-SO_2R_{10}$;

Ar is an optionally substituted $C_{5-20}$ aryl group;

M is a transition metal atom, such as ruthenium;

Q is hydrogen, a coordinating group, such as Hal, or a non-coordinating counter ion, the dashed line represents a covalent bond when Q is hydrogen or a coordinating group, or the dashed line represents an ionic bond when Q is a non-coordinating counter ion;

and salts thereof.

In another aspect of the invention there is provided a method for preparing a complex of formula (X), the method comprising the steps of:

(ii) reacting an amide of formula (II) to form an amine compound of formula (I); and
(iii) reacting the amine compound of formula (I), optionally as an acid addition salt, with a transition metal compound, to form a complex of formula (X),
where the complex of formula (X) has the structure shown below:

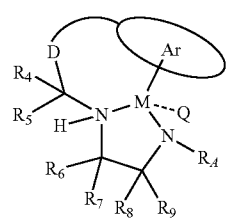

where D, $R_4$, $R_5$, $R_6$, $R_7$, $R_8$, and $R_9$, are as defined above for the compounds of formula (I), (Ia) and (Ib), and $R_A$ is $-SO_2R_{10}$;

Ar is an optionally substituted $C_{5-20}$ aryl group;

M is a transition metal atom, such as ruthenium;

Q is hydrogen, a coordinating group, such as Hal, or a non-coordinating counter ion, the dashed line represents a covalent bond when Q is hydrogen or a coordinating group, or the dashed line represents an ionic bond when Q is a non-coordinating counter ion;

and salts thereof.

In one embodiment, the method may comprise a first step of:

(i) preparing the amide of formula (II).

Where Q is hydrogen or a coordinating group, the complex of formula (X) has the structure shown below:

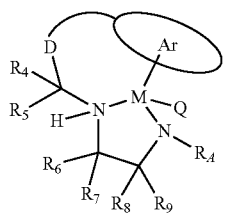

(X)

Where Q is a non-coordinating counter ion, the complex of formula (X) has the structure shown below:

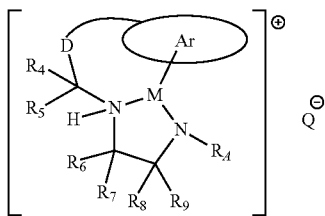

In group D the asterisk indicates the point of attachment to Ar in the complex of formula (X) and (XII).

In one embodiment, the reaction of amine (I) with a metal complex may proceed via the dimer of formula (XII), as described below:

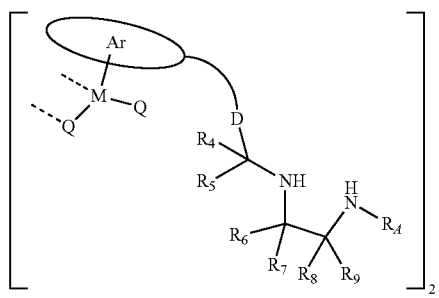

(XII)

where Ar, D, $R_4$, $R_5$, $R_6$, $R_7$, $R_8$, $R_9$, $R_A$, M and Q are as defined for the complex (X), and salts thereof.

When the counter ion is Hal, it may replaced with H by methods known in the art. Thus, in one embodiment, step (iii) yields a catalyst of formula (X) where Q is Hal, such as Cl, and the method includes the subsequent step (iv) of reacting (X) to form (XX), where (XX) has the structure shown below:

(XX)

where Ar, D, $R_4$, $R_5$, $R_6$, $R_7$, $R_8$, $R_9$, $R_A$, and M are as defined above for the complexes of formula (X).

In a fifth aspect there is provided a complex of formula (X) which is obtained or obtainable by the method of the second aspect of the invention.

In a sixth aspect of the invention there is provided a complex of formula (XI), where the complex of formula (XI) is a catalyst (XIa) or (XIb) having the structures shown below:

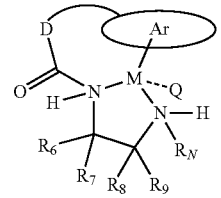

(XIa)

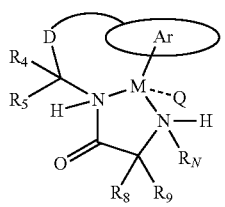

(XIb)

where Ar, D, $R_4$, $R_5$, $R_6$, $R_7$, $R_8$, $R_9$, Q and $R_N$ have the same meanings as the complexes of formula (X), and $R_N$ is hydrogen, straight, branched or cyclic $C_{1-10}$ alkyl.

In a seventh aspect of the present invention there is provided a method of preparing a complex of formula (XI), the method comprising the step of:

(i) reacting an amide compound of formula (II) where —$R_A$ is —$R_N$, optionally as an acid addition salt, with a transition metal compound, to form a complex of formula (XI).

In one embodiment, the reaction of amide (II) with a metal complex may proceed via the dimer of formula (XIII), as described below.

When the counter ion is Hal, it may be replaced with H. Thus, in one embodiment, step (ii) forms a complex of formula (XI) where Q is Hal, such as Cl, and the method includes the subsequent step (iii) of reacting (XI) to form (XXI), where (XXI) is a compound of formula (XXIa) or (XXIb) having the structures shown below:

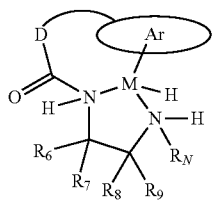

(XXIa)

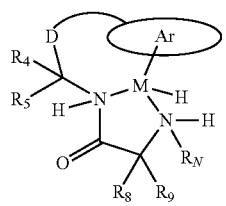

(XXIb)

where Ar, D, $R_6$, $R_7$, $R_8$, $R_9$, $R_N$ and M are as defined above for the complex of formula (X).

In one embodiment, the method further comprises the preliminary step of (i) preparing an amide of formula (II). The amide (II) may be prepared from a carboxylic acid (IV) and an amine (III), as described above according to step (i) in the first aspect of the invention.

The complexes of the invention may find use as catalysts.

Thus, in an eighth aspect of the invention there is provided a method of catalysis, the method comprising the step of:

(i) reacting a substrate comprising a carbon-heteroatom double bond in the presence of a complex of formula (X) or (XI).

The method may be a reduction reaction. In one embodiment, the method is the reduction of the substrate in the presence of gaseous hydrogen. In an alternative embodiment the method is a transfer hydrogenation reaction. In the latter case, hydrogen is formally added across the carbon-heteroatom double bond, however, gaseous hydrogen ($H_2$) is not the source.

In one embodiment, the method is for selectively hydrogenating a carbonyl group to provide the corresponding alcohol.

A hydrogenation may be stereoselective hydrogenation, achiral hydrogenation, achiral transfer hydrogenation or asymmetric transfer hydrogenation.

Also provided is the use of a complex of formula (X) or (XI) as a catalyst, including the use of the complex as a catalyst in a reaction described herein.

The invention also provides an amine of formula (I).

In one embodiment, the compound of formula (I) is a compound where Cy is an optionally substituted $C_{5-6}$ cycloalkadienyl group.

The invention also provides an amide of formula (II).

In one embodiment, the compound of formula (II) is a compound where Cy is an optionally substituted $C_{5-6}$ cycloalkadienyl group.

These and other aspects of the invention are described in further detail below.

DETAILED DESCRIPTION OF THE INVENTION

The present invention provides methods for preparing amine compounds of formula (I) for use as ligands in the complexes of formula (X), and methods for preparing complexes of formula (X) using the compounds of formula (I).

The amide (II) for use in the preparation of the amine (I) may itself be used as a ligand in a complex of formula (XI).

Ligands

An amine compound of formula (I) is a ligand for use in the preparation of a complex. The amine compound may be incorporated into a metal complex as a ligand. Amine compounds of formula (I) are described in the art for use as ligands in metal complexes, such as metal catalysts. In the present case, the amine compound of formula (I) is prepared from an amide of formula (II), which in turn may be prepared from an amine of formula (III) and a carboxylic acid of formula (IV). As noted above, amide (II) may also be used as a ligand in the preparation of a complex.

The methods of the invention react a carboxylic acid and an amine in an amide coupling reaction. Such are well known in the art. An activated carboxylic acid may be used in place of the carboxylic acid. Alternatively, an activated carboxylic acid may be generated from the carboxylic acid during the amide coupling reaction.

The methods of the invention react an aryl component (or a precursor aryl component, such as a cyclic diene) component and a sulfonamide component. The aryl component may have an amino functional group for reaction with a carboxylic acid functional group that is present in the sulfonamide component. Alternatively, the aryl component may have a carboxylic acid functional group for reaction with an amino acid functional group that is present in the sulfonamide component.

An amine compound of formula (I) is represented thus:

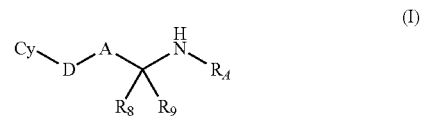

(I)

where:

A is *—$CH_2NHC(R_6R_7)$— or *—$C(R_4R_5)NHCH_2$—, where the asterisk indicates the point of attachment to D;

$R_4$ and $R_5$ are each independently selected from the group consisting of hydrogen, straight- or branched-chain $C_{1-20}$ alkyl, straight, branched or cyclic $C_{1-10}$ alkoxy, $C_{6-10}$ aryl and $C_{6-10}$ aryloxy, —OH, —CN, and —$CF_3$;

$R_6$, $R_7$, $R_8$ and $R_9$ are each independently selected from the group consisting of hydrogen, optionally substituted straight, branched or cyclic $C_{1-20}$ alkyl, optionally substituted straight, branched or cyclic $C_{1-20}$ alkoxy, optionally substituted $C_{6-20}$ aryl and optionally substituted $C_{6-20}$ aryloxy wherein the optional substituents are each independently selected from the group consisting of one or more straight, branched or cyclic $C_{1-20}$ alkyl, straight, branched or cyclic $C_{1-20}$ alkoxy, $C_{6-20}$ aryl, $C_{6-20}$ aryloxy, —OH, —CN, —$NR_{20}R_{21}$, —$COOR_{20}$, —$CONR_{20}R_{21}$ and —$CF_3$, or $R_6$ and $R_7$ together with the carbon atom to which they are bound and/or $R_8$ and $R_9$ together with the carbon atom to which they are bound form an optionally substituted $C_{3-20}$ cycloalkyl or an optionally substituted $C_{2-20}$ cycloalkoxy, wherein the optional substituents are each independently selected from the group consisting of one or more straight, branched or cyclic $C_{1-20}$ alkyl, straight, branched or cyclic $C_{1-20}$ alkoxy, $C_{6-20}$ aryl, $C_{6-20}$ aryloxy, —OH, —CN, —$NR_{20}R_{21}$, —$COOR_{20}$, —$CONR_{20}R_{21}$ and —$CF_3$, or one of $R_6$ and $R_7$ and one of $R_8$ and $R_9$ together form an optionally substituted $C_{5-10}$ cycloalkyl or an optionally substituted $C_{5-10}$ cycloalkoxy, wherein the optional substituents are each independently selected from the group consisting of one or more straight, branched or cyclic $C_{1-20}$ alkyl, straight, branched or cyclic $C_{1-20}$ alkoxy, $C_{6-20}$ aryl, $C_{6-20}$ aryloxy, —OH, —CN, —NR$_{20}$R$_{21}$, —COOR$_{20}$, —CONR$_{20}$R$_{21}$ and —CF$_3$;

D is an optionally substituted straight- or branched-chain $C_{1-4}$ alkyl group wherein the optional substituents are each independently selected from the group consisting of one or more straight, branched or cyclic $C_{1-10}$ alkyl, straight, branched or cyclic $C_{1-10}$ alkoxy, $C_{6-10}$ aryl, $C_{6-10}$ aryloxy, or D is a group:

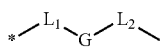

where $L_1$ is a covalent bond or optionally substituted $C_{1-3}$ alkyl; and $L_2$ is a covalent bond or optionally substituted $C_{1-2}$ alkyl;

where each optional substituent is a group independently selected from the list consisting of straight, branched or cyclic $C_{1-20}$ alkyl, straight, branched or cyclic $C_{1-20}$ alkoxy, $C_{6-20}$ aryl, $C_{6-20}$ aryloxy, —OH, —CN and —CF$_3$;

G is selected from —O—, —S—, and optionally substituted $C_{6-10}$ aryl, optionally substituted $C_{3-10}$ heteroaryl and optionally substituted $C_{6-10}$ cycloalkyl; and the optional substituents are selected from the list consisting of straight, branched or cyclic $C_{1-20}$ alkyl, straight, branched or cyclic $C_{1-20}$ alkoxy, $C_{6-20}$ aryl, $C_{6-20}$ aryloxy, —OH, —CN or —CF$_3$;

and the asterisk indicates the point of attachment to Cy;

Cy is optionally substituted $C_{6-20}$ aryl or optionally substituted $C_{5-6}$ cycloalkadienyl, where the optional substituents are selected from the list consisting of optionally substituted straight, branched or cyclic $C_{1-20}$ alkyl, optionally substituted straight, branched or cyclic $C_{1-20}$ alkoxy, optionally substituted $C_{6-20}$ aryl, optionally substituted $C_{6-20}$ aryloxy, —OH, CN, —NR$_{20}$R$_{21}$, —COOH, COOR$_{20}$, —CONH$_2$, —CONR$_{20}$R$_{21}$ and —CF$_3$ wherein the substituents are selected from the group consisting of one or more straight, branched or cyclic $C_{1-20}$ alkyl, straight, branched or cyclic $C_{1-20}$ alkoxy, $C_{6-20}$ aryl, $C_{6-20}$ aryloxy, —OH, —CN, —NR$_{30}$R$_{31}$, —COOR$_{30}$, —CONR$_{30}$R$_{31}$ and —CF$_3$;

$R_A$ is —SO$_2$R$_{10}$ or —R$_N$;

$R_{10}$ is hydrogen, an optionally substituted straight, branched or cyclic $C_{1-10}$ alkyl, an optionally substituted $C_{6-10}$ aryl or —NR$_{11}$R$_{12}$ wherein the optional substituents are each independently selected from the group consisting of one or more straight, branched or cyclic $C_{1-10}$ alkyl, straight, branched or cyclic $C_{1-10}$ alkoxy, $C_{6-10}$ aryl, $C_{6-10}$ aryloxy, -Hal, —OH, —CN, —NR$_{20}$R$_{21}$, —COOR$_{20}$, —CONR$_{20}$R$_{21}$ and —CF$_3$;

$R_N$ is hydrogen, or straight, branched or cyclic $C_{1-10}$ alkyl;

$R_{11}$ and $R_{12}$ are independently selected from the group consisting of hydrogen, optionally substituted straight, branched or cyclic $C_{1-10}$ alkyl and optionally substituted $C_{6-10}$ aryl, wherein the substituents are selected from the group consisting of one or more straight, branched or cyclic $C_{1-10}$ alkyl groups, straight, branched or cyclic $C_{1-10}$ alkoxy, $C_{6-10}$ aryl, $C_{6-10}$ aryloxy, —OH, —CN, —NR$_{20}$R$_{21}$, —COOR$_{20}$, —CONR$_{20}$R$_{21}$ and —CF$_3$, or $R_{11}$ and $R_{12}$ together with the nitrogen atom to which they are bound form an optionally substituted $C_{2-10}$ cycloalkyl-amino group wherein the substituents are selected from the group consisting of one or more straight, branched or cyclic $C_{1-10}$ alkyl, straight, branched or cyclic $C_{1-10}$ alkoxy, $C_{6-10}$ aryl, $C_{6-10}$ aryloxy, —OH, —CN, —NR$_{20}$R$_{21}$, —COOR$_{20}$, —CONR$_{20}$R$_{21}$ and —CF$_3$;

$R_{20}$ and $R_{21}$ are each independently selected from the group consisting of hydrogen, optionally substituted straight, branched or cyclic $C_{1-20}$ alkyl, optionally substituted straight, branched or cyclic $C_{1-20}$ alkoxy, optionally substituted $C_{6-20}$ aryl, optionally substituted $C_{6-20}$ aryloxy, —OH, —CN, —NR$_{30}$R$_{31}$, —COOR$_{30}$, —CONR$_{30}$R$_{31}$ and —CF$_3$, wherein the substituents are selected from the group consisting of one or more straight, branched or cyclic $C_{1-20}$ alkyl, straight, branched or cyclic $C_{1-20}$ alkoxy, $C_{6-20}$ aryl, $C_{6-20}$ aryloxy, —OH, —CN and —CF$_3$; and $R_{30}$ and $R_{31}$ are each independently selected from the group consisting of hydrogen, optionally substituted straight, branched or cyclic $C_{1-20}$ alkyl, optionally substituted straight, branched or cyclic $C_{1-20}$ alkoxy, optionally substituted $C_{6-20}$ aryl, optionally substituted $C_{6-20}$ aryloxy, —OH, —CN and —CF$_3$, wherein the substituents are selected from the group consisting of one or more straight, branched or cyclic $C_{1-20}$ alkyl, straight, branched or cyclic $C_{1-20}$ alkoxy, $C_{6-20}$ aryl, $C_{6-20}$ aryloxy, —OH, —CN and —CF$_3$;

and salts thereof.

In one embodiment, $R_A$ is —SO$_2$R$_{10}$. In one embodiment, $R_A$ is —R$_N$.

In one embodiment, the amine compound (I) is a compound (Ia):

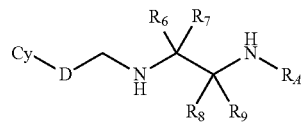

For example, compound (Ia) may be a compound of formula (Ic):

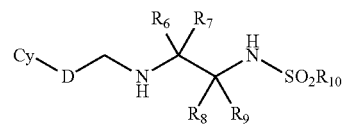

In one embodiment, the amine compound (I) is a compound (Ib):

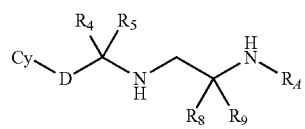

For example, compound (Ia) may be a compound of formula (Id):

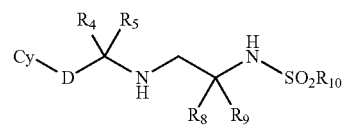

The carbon atoms to which $R_6$ and $R_7$, and $R_8$ and $R_9$ (where they are not the same) are bound may be asymmetric. The amine of formula (I) therefore may be chiral and this ligand may be used to prepare chiral complexes, which may be used as chiral catalysts. The hydrogenation processes described herein therefore include asymmetric hydrogenation processes. Thus complexes for use as chiral catalysts, and asymmetric hydrogenation processes are within the scope of the invention.

In one embodiment, G is —O— or —S— only when $L^2$ is $C_{1-2}$ alkyl.

The amide compound of formula (II) is represented thus:

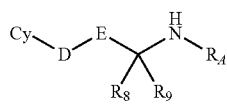

(II)

where:

E is *—C(O)NHC($R_6R_7$)— or *—C($R_4R_5$)NHC(O)—, where the asterisk indicates the point of attachment to D; and Cy, D, $R_4$, $R_5$, $R_6$, $R_7$, $R_8$, $R_9$ and $R_A$ are as described above for the amine compounds of formula (I), and salts thereof.

In one embodiment, $R_A$ is —$SO_2R_{10}$.

In one embodiment, $R_A$ is —$R_N$.

In one embodiment, the amide compound (II) is a compound (IIa):

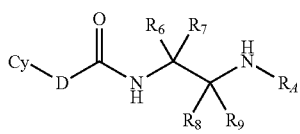

In one embodiment, the amide compound (II) is a compound (IIc):

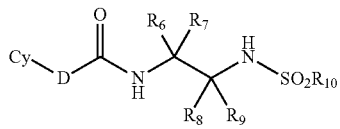

In one embodiment, the amide compound (II) is a compound (IIb):

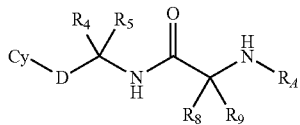

In one embodiment, the amide compound (II) is a compound (IId):

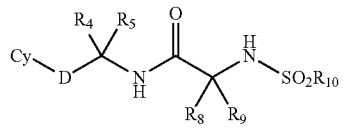

The amide (II) may be prepared from an amine (III), which is selected from (IIIa) or (IIIb), where (IIIa) is represented thus:

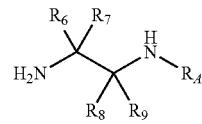

where $R_6$, $R_7$, $R_8$, $R_9$ and $R_A$ are as described above for the amine compounds of formula (I), and salts thereof, and (IIIb) is represented thus:

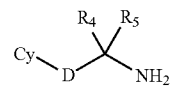

where Cy, D, $R_4$, and $R_5$ are as described above for the amine compounds of formula (I), and salts thereof.

The amine (III) may be used in a reaction with a carboxylic acid (IV), which is selected from (IVa) or (IVb), where (IVa) is represented thus:

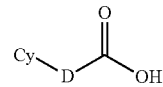

where Cy and D are as described above for the amine compounds of formula (I), and salts and activated forms thereof, and (IVb) is represented thus:

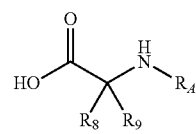

where $R_8$, $R_9$ and $R_A$ are as described above for the amine compounds of formula (I), and salts and activated forms thereof.

In one embodiment, amine (IIIa) is reacted with carboxylic acid (IVa) to form amide (II).

In one embodiment, amine (IIIb) is reacted with carboxylic acid (IVb) to form amide (II).

The present invention also provides the amine compound of formula (I) and the amide compound of formula (II), and salts thereof, which may be obtained or obtainable by the methods describe herein.

The substituent groups are discussed further below.

A

In one embodiment, A is *—$CH_2NHC(R_6R_7)$—.

In one embodiment, A is *—$C(R_4R_5)NHCH_2$—.

E

In one embodiment, E is *—C(O)NHC($R_6R_7$)—.

In one embodiment, E is *—C($R_4R_5$)NHC(O)—.

Cy

The group Cy may be an optionally substituted aryl group. The aryl group may be a $C_{6-10}$ aryl group.

In one embodiment, Cy is optionally substituted phenyl or napthyl.

In one embodiment, Cy is optionally substituted phenyl, for example unsubstituted phenyl.

In one embodiment, Cy is optionally substituted $C_{5-6}$ cycloalkadienyl.

In one embodiment, Cy is optionally substituted cyclohexadienyl, such as unsubstituted cyclohexadienyl.

The cyclohexadienyl group may be a cyclohexa-1,4-dienyl, cyclohexa-2,5-dienyl, cyclohexa-1,3-dienyl or cyclohexa-2,4-dienyl group, such as cyclohexa-1,4-dienyl.

In one embodiment, Cy is optionally substituted cyclopentadienyl, such as unsubstituted cyclopentadienyl or pentamethylcyclopentadienyl.

The cyclopentadienyl group may be a cyclopenta-2,4-dienyl, cyclopenta-1,4-dienyl or cyclopenta-1,3-dienyl group.

In one embodiment, Cy is optionally substituted with one or more groups selected from the list consisting of straight- or branched-chain $C_{1-10}$ alkyl, straight- or branched-chain $C_{1-10}$ alkoxy, $C_{6-10}$ aryl, $C_{6-10}$ aryloxy and —OH.

In one embodiment, Cy is optionally substituted with one or more groups selected from the list consisting of straight-chain $C_{1-10}$ alkyl and branched-chain $C_{1-10}$ alkyl, such as methyl, ethyl, n-propyl, i-propyl, n-butyl, i-butyl, s-butyl and t-butyl.

D

In one embodiment, D is an optionally substituted straight- or branched-chain $C_{1-4}$ alkyl, such as an optionally substituted straight- or branched-chain $C_{2-4}$ alkyl, wherein the substituents are selected from the group consisting of straight- or branched-chain $C_{1}10$ alkyl, straight- or branched-chain $C_{1-10}$ alkoxy, $C_{6-10}$ aryl and $C_{6-10}$ aryloxy.

In one embodiment, D is —$CH_2$—, —$(CH_2)_2$—, —$(CH_2)_3$— or —$(CH_2)_4$—.

In one embodiment, D is —$(CH_2)_2$— or —$(CH_2)_3$—

In one embodiment, D is —$(CH_2)_2$—.

In one embodiment, D is a group:

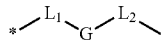

In one embodiment, one of $L_1$ and $L_2$ is not a covalent bond.

In one embodiment, $L_1$ is —$CH_2$—.

In one embodiment, $L_2$ is —$CH_2$—.

In one embodiment, one of $L_1$ and $L_2$ is —$CH_2$— and the other of $L_1$ and $L_2$ is a covalent bond.

G may be optionally substituted $C_{6-10}$ aryl, such as:

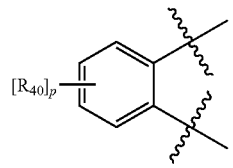

where p is an integer selected from 0, 1, 2, 3 or 4;

the or each $R_{40}$ is independently selected from the group consisting of hydrogen, straight, branched or cyclic $C_{1-20}$ alkyl, straight, branched or cyclic $C_{1-20}$ alkoxy, $C_{6-20}$ aryl, $C_{6-20}$ aryloxy, —OH, —CN or —$CF_3$.

In one embodiment, G is unsubstituted phenyl.

G may be an optionally substituted cycloalkyl group, such as optionally substituted cyclohexyl or cyclopentyl, such as:

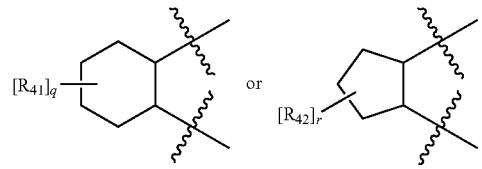

where q is an integer selected from 0, 1, 2, 3 or 4;

r is an integer selected from 0, 1, 2 or 3;

the or each $R_{41}$ is independently selected from the group consisting of hydrogen, straight, branched or cyclic $C_{1-20}$ alkyl, straight, branched or cyclic $C_{1-20}$ alkoxy, $C_{6-20}$ aryl, $C_{6-20}$ aryloxy, —OH, —CN or —$CF_3$;

the or each $R_{42}$ is independently selected from the group consisting of hydrogen, straight, branched or cyclic $C_{1-20}$ alkyl, straight, branched or cyclic $C_{1-20}$ alkoxy, $C_{6-20}$ aryl, $C_{6-20}$ aryloxy, —OH, —CN or —$CF_3$.

In one embodiment, G is —O— or —S—. In this embodiment, it is preferred that $L_2$ is optionally substituted $C_{1-2}$ alkyl.

$R_4$ and $R_5$

In one embodiment, $R_4$ and $R_5$ are independently selected from the group consisting of hydrogen, straight- or branched-chain $C_{1-20}$ alkyl, straight, branched or cyclic $C_{1-10}$ alkoxy, $C_{6-10}$ aryl and $C_{6-10}$ aryloxy.

In one embodiment, $R_4$ and $R_5$ are independently selected from the group consisting of straight, branched or cyclic $C_{1-20}$ alkyl, straight, branched or cyclic $C_{1-20}$ alkoxy, $C_{6-20}$ aryl, $C_{6-20}$ aryloxy, —OH, —CN and —$CF_3$.

In one embodiment, $R_4$ and $R_5$ are each hydrogen.

In one embodiment, $R_4$ and $R_5$ are each independently selected from the group consisting of straight- or branched-chain $C_{1-10}$ alkyl, straight- or branched-chain $C_{1-10}$ alkoxy, $C_{6-10}$ aryl and $C_{6-10}$ aryloxy.

In one embodiment, $R_4$ and $R_5$ are each independently selected from hydrogen, straight-chain $C_{1-10}$ alkyl and branched-chain $C_{1-10}$ alkyl.

In one embodiment, $R_4$ and $R_5$ are each independently selected from hydrogen, methyl, ethyl, n-propyl, i-propyl, n-butyl, i-butyl, s-butyl and t-butyl.

Re, $R_7$, $R_8$ and $R_9$

In one embodiment, $R_6$, $R_7$, $R_8$ and $R_9$ are each independently selected from the group consisting of hydrogen, optionally substituted straight- or branched-chain $C_{1-10}$ alkyl, optionally substituted straight- or branched-chain $C_{1-10}$ alkoxy, optionally substituted $C_{6-10}$ aryl and optionally substituted $C_{6-10}$ aryloxy wherein the substituents are selected from the group consisting of straight- or branched-chain $C_{1-10}$ alkyl, straight- or branched-chain $C_{1-10}$ alkoxy, $C_{6-10}$ aryl, $C_{6-10}$ aryloxy and —OH.

In one embodiment, the groups $R_6$, $R_7$, $R_8$ and $R_9$ are each independently selected from the group consisting of hydrogen and optionally substituted $C_{6-10}$ aryl.

In one embodiment, $R_6$, $R_7$, $R_8$ and $R_9$ are each independently selected from the group consisting of hydrogen and optionally substituted phenyl. Preferably, one of $R_6$ and $R_7$ is phenyl and the other of $R_6$ and $R_7$ is hydrogen. Preferably, one of $R_8$ and $R_9$ is phenyl and the other of $R_8$ and $R_9$ is hydrogen.

In one embodiment, $R_6$ and $R_9$ are the same. In one embodiment, $R_6$ and $R_9$ are each phenyl.

In one embodiment, $R_7$ and $R_8$ are the same. In one embodiment, $R_7$ and $R_8$ are each hydrogen.

In one embodiment, $R_6$ and $R_7$ are each hydrogen. In one embodiment, $R_8$ and $R_9$ are each hydrogen.

In one embodiment, $R_6$, $R_7$, $R_8$ and $R_9$ are each hydrogen.

In another embodiment, $R_6$ and $R_7$ together with the carbon atom to which they are bound and/or $R_8$ and $R_9$ together with the carbon atom to which they are bound form an optionally substituted $C_{5-10}$ cycloalkyl or an optionally substituted $C_{4-10}$ cycloalkoxy, wherein the substituents are selected from the group consisting of straight- or branched-chain $C_{1-10}$, straight- or branched-chain $C_{1-10}$ alkoxy, $C_{6-10}$ aryl, $C_{6-10}$ aryloxy and —OH.

In yet another embodiment, one of $R_6$ and $R_7$ and one of $R_8$ and $R_9$ together form an optionally substituted $C_{5-10}$ cycloalkyl or an optionally substituted $C_{5-10}$ cycloalkoxy, wherein the substituents are selected from the group consisting of straight- or branched-chain $C_{1-10}$ alkyl, straight- or branched-chain $C_{1-10}$ alkoxy, $C_{6-10}$ aryl, $C_{6-10}$ aryloxy and —OH.

$R_4$

In one embodiment, $R_4$ is —$SO_2R_{10}$

In another embodiment, $R_4$ is —$R_N$.

$R_{10}$

The group $R_{10}$ may have one or more stereogenic centres. For example, $R_{10}$ may be or include a branched or substituted alkyl group where the branch point or the substituent positions is a stereogenic centre. The stereogenic centres may be provided in a group $R_{11}$ or $R_{12}$. A stereogenic group within $R_{10}$ may be provided in addition to any stereogenic centres at other locations within the compound (for example, in addition to stereogenic centres that may be provided at the carbon atoms to which groups $R_6$ and $R_7$ or $R_8$ and $R_9$ are bound).

In one embodiment, $R_{10}$ is hydrogen, an optionally substituted straight, branched or cyclic $C_{1-10}$ alkyl, an optionally substituted $C_{6-10}$ aryl wherein the substituents are selected from the group consisting of one or more straight, branched or cyclic $C_{1-10}$ alkyl, straight, branched or cyclic $C_{1-10}$ alkoxy, $C_{6-10}$ aryl, $C_{6-10}$ aryloxy, -Hal, —OH, —CN, —$NR_{20}R_{21}$, —$COOR_{20}$, —$CONR_{20}R_{21}$ and —$CF_3$.

In another embodiment, the substituents are selected from the group consisting of one or more hydrogen, straight, branched or cyclic $C_{1-10}$ alkyl, straight, branched or cyclic $C_{1-10}$ alkoxy, $C_{6-10}$ aryl, $C_{6-10}$ aryloxy, -Hal, or —$CF_3$. In another embodiment, $R_{10}$ is a straight- or branched-chain $C_{1-10}$ alkyl or a $C_{6-10}$ aryl optionally substituted with one or more straight- or branched-chain $C_{1-10}$ alkyl groups.

In one embodiment, $R_{10}$ is selected from hydrogen, $C_{1-10}$ alkyl, $C_{6-10}$ aryl optionally substituted with $C_{1-10}$ alkyl.

Examples of $R_{10}$ include, but are not limited to, 4-methylphenyl (p-tolyl), methyl, 4-methoxyphenyl, 4-chlorophenyl, trifluoromethyl, 3,5-dimethylphenyl, 2,4,6-trimethylphenyl, 2,4,6-triisopropylphenyl, 4-tert-butylphenyl, pentamethylphenyl, pentafluorophenyl and 2-naphthyl.

In one embodiment, $R_{10}$ is selected from methyl and 4-methyl-phenyl. In these embodiments, —$SO_2$—$R_{10}$ may be referred to as mesyl and tosyl respectively.

In another embodiment, $R_{10}$ is —$NR_{11}R_{12}$ wherein $R_{11}$ and $R_{12}$ are independently selected from the group consisting of hydrogen, straight- or branched-chain $C_{1-10}$ alkyl and $C_{6-10}$ aryl optionally substituted with one or more straight- or branched-chain $C_{1-10}$ alkyl groups.

In one embodiment, $R_{10}$ is —$NMe_2$.

In one embodiment, $R_{10}$ is selected from the group consisting of —$NMe_2$, pentafluorophenyl, methyl, 4-methyl-phenyl, 2,4,6-trimethylphenyl, and 2,4,6-triisopropylphenyl.

$R_N$

In one embodiment, $R_N$ is hydrogen.

Ligand Preparation

In a first aspect of the invention there is provided a method of preparing an amine compound of formula (I), the method comprising the steps of:
  (i) preparing an amide of formula (II); and
  (ii) reacting the amide of formula (II) to the amine compound of formula (I).

In a second aspect of the invention there is provided a method of preparing an amine compound of formula (I), the method comprising the step of:
  (ii) reacting an amide of formula (II) to the amine compound of formula (I).

The compounds of formula (I) and (II) are described above.

In one embodiment, the amide (II) is reduced to the amine (I) in step (ii).

A reducing agent may be used, such as a metal hydride. Alternatively the amide may be reduced in the presence of a catalyst, such as a metal catalyst, for example with hydrogen gas.

The reducing agent may be an aluminium hydride-based reducing agent.

In one embodiment, when Cy is an aryl or cyclohexyldienyl group, the reducing agent may be selected from the group consisting of lithium aluminium hydride ($LiAlH_4$), $LiAlH(OMe)_3$, $LiAlH(OEt)_3$, $AlH_3$, $BH_3$.THF (borane tetrahydrofuran complex) solution, $BH_3$.DMS (borane dimethyl sulfide complex) solution and $B_2H_6$. In one embodiment, when Cy is a cyclohexyldienyl group, the reducing agent may be selected from the group consisting of $LiAlH_4$, $LiAlH(OMe)_3$, $LiAlH(OEt)_3$ and $AlH_3$.

In one embodiment, the reducing agent is $LiAlH_4$.

Where a catalyst is used, the reaction may be a heterogeneous or homogeneous catalysis reaction.

In one embodiment, the reduction reaction is performed in an organic solvent.

The organic solvent may be an ether solvent, such as THF or MTBE.

In one embodiment, step (ii) is performed at temperatures between about −78° C. to about 100° C., such as about −10° C. to about 100° C., such as about 0° C. to about −10° C.

In one embodiment, step (ii) includes heating the reaction mixture to at least 30° C., at least 50° C. or at least 60° C.

Where a reducing agent is used, the reducing agent may be mixed with the amide (I) at a temperature below room temperature, such as about 0° C. or less. The reaction mixture may subsequently be warmed to room temperature or above, such as heated to a temperature as described above.

In one embodiment, step (i) comprises the preparation of the amide of formula (II) from an amine of formula (III) and a carboxylic acid of formula (IV). The carboxylic acid may be an activated carboxylic acid, such as an acid chloride or an activated ester. The activated carboxylic acid may be generated in situ from the carboxylic acid. Amide (III) and carboxylic (IV) are as defined above.

In one embodiment, the reaction of a carboxylic acid with an amine may be undertaken in the presence of one or more amide coupling reagents, as are well known in the art. A coupling reagent may optionally be used together with a base, such as an organic base.

Amide coupling reagents suitable for use include carbodiimides (e.g. EDC and DCC), phosphonium salts (e.g. PyBOP), and uranium and guanidinium salts (e.g. HATU and HBTU), such as described in further detail below.

A carbodiimide may include dicyclohexylcarbodiimide (DCC), N-(3-dimethylaminopropyl)-N'-ethylcarbo-diimide (EDC), 1-tert-butyl-3-ethylcarbodiimide, N-cyclohexyl-N'-2-morpholinoethyl)carbodiimide, and diisopropylcarbodiimide.

A phosphonium salt may include benzotriazol-1-yl-oxytripyrrolidinophosphonium hexafluorophosphate (PyBoP), (7-Azabenzotriazol-1-yloxy)tripyrrolidinophosphonium hexafluorophosphate (PyAOP) and chlorotripyrrolidinophosphonium hexafluorophosphate (PyBroP).

Uranium and guanidinium salts include O-(Benzotriazol-1-yl)-N,N,N',N'-tetramethyluronium hexafluorophosphate (HBTU), O-(Benzotriazol-1-yl)-N,N,N',N'-tetramethyluronium tetrafluoroborate (TBTU), O-(7-Azabenzotriazol-1-yl)-N,N,N',N'-tetramethyluronium hexafluorophosphate (HATU), N,N,N',N'-tetramethyl-O—(N-succinimidyl)uronium tetrafluoroborate (TSTU) and O-[(ethoxycarbonyl)cyanomethylenamino]-N,N,N',N'-tetramethyluronium tetrafluoroborate (TNTU), amongst others.

Other agents may be used, including other benzotriazole-containing agents such as N-hydroxybenzotriazole (HOBt) and 1-hydroxy-7-azabenzotriazole (HOAt), or reagents such as 1-(mesitylene-2-sulfonyl)-3-nitro-1,2,4-triazole (MSNT) and propylphosphonic anhydride (T3P).

Example coupling reagents are available from commercial sources, for example as described in *ChemFiles* 2007, 4, No. 2, Sigma-Aldrich.

As noted above, the reaction of the acid and the carboxylic acid may be conducted in the presence of a base. Example bases include alkylamine bases such as N,N-diisopropylethylamine (DIPEA) and triethylamine (TEA), 4-dimethylaminopyridine (DMAP), pyridine, and N-methylmorpholine (NMM).

The amide-forming reaction may be performed in a solvent or solvent mixture. A solvent for use may include dimethylformamide (DMF) and dichloromethane (DCM), toluene and acetonitrile. Other solvents, such as other alkyl formamides, halogenated hydrocarbons, aromatic hydrocarbons and nitriles may be used as required.

The amide forming reaction may be performed at room temperature, such as a temperature selected from the range 10 to 25° C.

In one embodiment, two or more of the reagents used in the amide synthesis may be brought together at reduced temperature, such as below room temperature, for example at a temperature of 4° C. or less, such as 0° C. or less. After the addition of the two or more reagents, the reaction mixture may be permitted to warm to room temperature.

The carboxylic acid compound used in the amide forming reaction may be initially reacted with the amide coupling reagents to pre-form an activated form of the carboxylic acid. The amine compound may then be subsequently added to the reaction mixture. This is not essential, and the reaction components may be mixed in an alternative sequence, such as described in the worked examples herein.

In one embodiment, an activated carboxylic acid of formula (V) may be used in place of a carboxylic acid of formula (IV), where (V) is selected from (Va) and (Vb), where (Va) is represented thus:

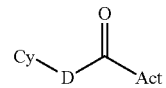

where Cy and D are as described above for the amine compounds of formula (I), Act is an activating group, and salts thereof, and (Vb) is represented thus:

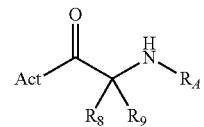

where $R_8$, $R_9$ and $R_A$ are as described above for the amine compounds of formula (I), Act is an activating group, and salts and activated forms thereof.

In one embodiment, (Va) may react with (IVb) to form (II).

In one embodiment, (Vb) may react with (IIIb) to form (II).

Compound (V) may be an acyl halide, a haloformate, an anhydride or a carboxylic ester.

Accordingly, in one embodiment, Act is halo, haloformate (—OC(O)Hal), —OC(O)$R^{Act}$ or —O$R^{Act}$, where $R^{Act}$ is an optionally substituted straight, branched or cyclic $C_{1-10}$ alkyl, an optionally substituted $C_{6-10}$ aryl or optionally substituted $C_{5-10}$ heteroaryl group.

The carboxylic acid (IV) may be reacted to form an acyl halide, haloformate, anhydride or carboxylic ester by methods known in the art Where Act is halo, such as Cl, the compound may be referred to as an acid halide, such as an acid chloride. The acid halide may be prepared from the corresponding carboxylic acid, for example using 1-chloro-N,N,2-trimethyl-1-propenylamine, chloro-N,N,N',N'-bis(tetramethylene)formamidinium tetrafluoroborate and chloro-N,N,N',N'-bis(tetramethylene)formamidinium hexafluorophosphate, chloro-N,N,N',N'-tetramethylformamidinium hexafluorophosphate and fluoro-N,N,N',N'-tetramethylformamidinium hexafluorophosphate.

The methods described above may be performed under an inert atmosphere, such as an argon or nitrogen atmosphere.

Complexes

In one aspect of the invention there is provided a complex of formula (X) which is obtained or obtainable from the method of the invention.

In a further aspect of the invention there is provided a complex of formula (XI). The catalyst is obtained or obtainable from the reaction of an amide (II) with a metal complex.

The catalyst of formula (XI) is an alternative to the complex of formula (X), and may be used in place of, or in combination with, the complex of formula (X) in a method of synthesis, such as described herein.

The complex of formula (X) is represented thus:

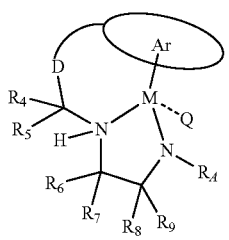

where D, $R_4$, $R_5$, $R_6$, $R_7$, $R_8$, and $R_9$, are as defined for the amine of formula (I), except that $R_4$ and $R_5$ are each hydrogen and/or $R_6$ and $R_7$ are each hydrogen, and $R_A$ is $-SO_2R_{10}$;

Q is hydrogen, a coordinating group, such as Hal, or a non-coordinating counter ion, the dashed line represents a covalent bond when Q is hydrogen or a coordinating group, or the dashed line represents an ionic bond when Q is a non-coordinating counter ion;

M is a transition metal atom, such as ruthenium; and

Ar is a $C_{5-20}$ aryl group covalently attached to D and bonded to the metal atom, where the aryl group is optionally substituted with one or more groups selected from the list consisting of optionally substituted straight, branched or cyclic $C_{1-20}$ alkyl, optionally substituted straight, branched or cyclic $C_{1-20}$ alkoxy, optionally substituted $C_{6-20}$ aryl, optionally substituted $C_{6-20}$ aryloxy, $-OH$, CN, $-NR_{20}R_{21}$, $-COOH$, $COOR_{20}$, $-CONH_2$, $-CONR_{20}R_{21}$ and $-CF_3$ wherein the substituents are selected from the group consisting of one or more straight, branched or cyclic $C_{1-20}$ alkyl, straight, branched or cyclic $C_{1-20}$ alkoxy, $C_{6-20}$ aryl, $C_{6-20}$ aryloxy, $-OH$, $-CN$, $-NR_{30}R_{31}$, $-COOR_{30}$, $-CONR_{30}R_{31}$ and $-CF_3$ and salts thereof.

The complex may be in salt form with an appropriate counter ion, typically a counter anion. The salt may be a chloride ($Cl^-$), bromide ($Br^-$), phosphate ($PO_4^{3-}$), tetrafluoroborate ($BF_4^-$), sulfate ($SO_3^{2-}$), chloroborate, triflate ($CF_3SO_3^-$), or hexafluorophosphate ($PF_6^-$).

Ar

In one embodiment, the aryl group is a $C_{5-10}$ aryl group, such as a $C_5$ or $C_6$ aryl group. Thus the aryl group may be a $\eta_5$ or $\eta_6$ aryl group ligand.

In one embodiment, the aryl group is phenyl, optionally substituted as described above. In this embodiment, the structure of the complex may be represented thus:

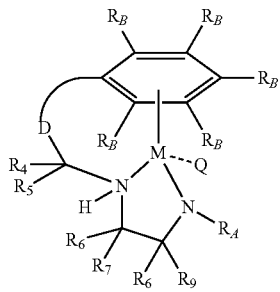

where each $R_B$ is independently hydrogen or optionally substituted straight, branched or cyclic $C_{1-20}$ alkyl, optionally substituted straight, branched or cyclic $C_{1-20}$ alkoxy, optionally substituted $C_{6-20}$ aryl, optionally substituted $C_{6-20}$ aryloxy, $-OH$, CN, $-NR_{20}R_{21}$, $-COOH$, $COOR_{20}$, $-CONH_2$, $-CONR_{20}R_{21}$ and $-CF_3$ wherein the optional substituents are each independently selected from the group consisting of one or more straight, branched or cyclic $C_{1-20}$ alkyl, straight, branched or cyclic $C_{1-20}$ alkoxy, $C_{6-20}$ aryl, $C_{6-20}$ aryloxy, $-OH$, $-CN$, $-NR_{30}R_{31}$, $-COOR_{30}$, $-CONR_{30}R_{31}$ and $-CF_3$.

In one embodiment, each $R_B$ is independently selected from the group consisting of hydrogen, straight-chain $C_{1-10}$ alkyl and branched-chain $C_{1-10}$ alkyl. More preferably, each $R_B$ is independently selected from the group consisting of hydrogen, methyl, ethyl, n-propyl, i-propyl, n-butyl, i-butyl, s-butyl and t-butyl. Most preferably, each $R_B$ is hydrogen.

M

M is a transition metal atom.

In one embodiment, the metal is selected from the group consisting of ruthenium, rhodium, osmium, and iridium.

In one embodiment, the metal is ruthenium.

Where M is rhodium or iridium the group Ar may be a $C_5$ aryl ring ($\eta_5$), such as $C_5$ aryl ring derived from an optionally substituted cyclopentadienyl.

Where M is ruthenium or osmium, and the group Ar is a $C_5$ aryl ring, no counter ion is present in the complex.

Q

Each Q is a coordinating group or non-coordinating counter ion.

In one embodiment, Q is a coordinating group, such as $-H$, $-Cl$, $-Br-$ or $-I$, preferably $-H$ or $-Cl$, most preferably $-Cl$.

In one embodiment, Q is a non-coordinating counter ion, such as $BF_4-$, $BF_6-$ and $CF_3SO_3$-(triflate).

Complex Preparation

A complex of the invention may be prepared by reacting a ligand, such as (I) or (II), with an appropriate transition metal compound. The transition metal compound may be a transition metal salt, complex or metal precursor.

Complexes of formula (X) are known in the art, and their preparation from amine compounds of formula (I), where $R_A$ is $-SO_2R_{10}$, and metal complexes is also known. See, for example, the work of Hayes et al., WO 2010/106364 and WO 2014/068331.

In one embodiment, a complex (X) may be prepared from a diene-containing amine (I) where $R_A$ is $-SO_2R_{10}$. In one embodiment, a complex (XI) may be prepared from a diene-containing amide (II). These are compounds where Cy is a cycloalkadienyl group, such as a cyclohexyldienyl group.

In this embodiment, a diene-containing amine (I) or a diene-containing amide (II) is reacted with a metal compound, to form a complex of formula (X) or (XI) respectively.

In one embodiment, a complex (X) may be prepared from an aryl-containing amine (I), where $R_A$ is $-SO_2R_{10}$. In one embodiment, a complex (XI) may be prepared from an aryl-containing amide (II). These are compounds where Cy is an aryl group, such as a phenyl group.

The transition metal compound may be a metal halide, such as $MHal_3$, where M and Hal are as described for the complex of formula (X).

In one embodiment, the transition metal compound is $RuHal_3$, such as $RuCl_3$.

In one embodiment, the transition metal compound is provided in an aqueous acidic solution, such as an aqueous acidic solution of $RuCl_3$.

In one embodiment, the method may comprise the preliminary step of treating the amine (I) or amide (II) with an acid, to generate the acid addition salt of (I) and (II). The acid addition salt of (I) and (II) may then be reacted with a transition metal compound to yield the complex of formula (X) or (XI). The amide (II) may be reacted with an acid when the group $R_A$ is $R_N$.

A base may be added to a reaction mixture comprising transition metal compound and the acid addition salt of (I) and (II).

In this embodiment, an aryl-containing amine (I) or an aryl-containing amide (II) is reacted with a transition metal compound, to form a complex of formula (X) or (XI) respectively.

The transition metal compound may be an arene metal complex, such as a complex $[MHal_2(Ar)]_2$, where M and Hal are as described for the complex of formula (X) and Ar is an aryl group.

In one embodiment, the transition metal compound is a transition metal compound of formula (IIa) or (IIb) as described in WO 2014/068331, the contents of which are hereby incorporated by reference in their entirety.

In one embodiment, the transition metal compound is $[RuCl_2(C_6H_5CO_2Et)]_2$.

In one embodiment, the preparation of the complex (X) may proceed via the intermediate dimer of formula (XII), which is represented thus:

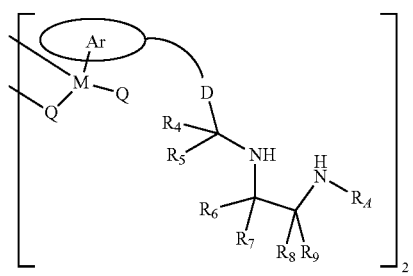

(XII)

where Ar, D, $R_4$, $R_5$, $R_6$, $R_7$, $R_8$, $R_9$, $R_{10}$, M and Q are as defined for the complex (X), and salts thereof.

Similarly, the preparation of the complex (XI) may proceed via the intermediate dimer compound of formula (XIII), which is selected from (XIIIa) and (XIIIb), which are represented thus:

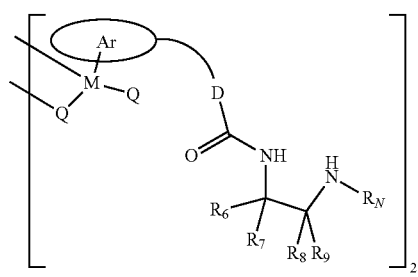

(XIIIa)

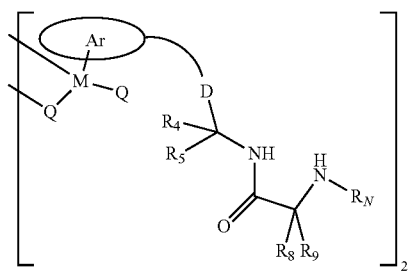

(XIIIb)

where Ar, D, $R_4$, $R_5$, $R_6$, $R_7$, $R_8$, $R_9$, $R_N$, M and Q are as defined for the complex (XI), and salts thereof.

The dimer is believed to have a structure where a Q group from each monomer is a bridging ligand between M atoms. The bonding between the monomers is shown as dashed bonds in the chemical structures of the dimer form.

A dimer may itself be used as a catalyst in a reduction reaction. The dimer may convert to the monomer form during the reduction reaction.

Thus, it follows that the reaction product of a reaction between an aryl-containing amine (I) or an aryl-containing amide (II) with a transition metal compound may be used as a catalyst in a reduction reaction.

The intermediate dimer of formula (XII) or (XIII) may be converted to the complex (X) or (XI) in the presence of a base, such as an organic base, for example, $^i$-$Pr_2EtN$ or triethylamine. The reaction of (XII) or (XIII) may include heating the dimer, for example to at least 30° C., at least 50° C. or at least 60° C.

Other methods for the preparation of a complex from a compound of formula (X) or (XI) may be employed.

A complex of formula (X) may be converted to a complex of formula (XX):

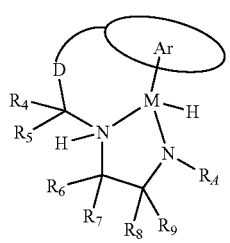

(XX)

where Ar, D, $R_4$, $R_5$, $R_6$, $R_7$, $R_8$, $R_9$, and M are as defined above for the complexes of formula (X), and $R_A$ is $-SO_2R_{10}$.

A complex of formula (X) may be reacted with a hydrogen donor to yield (XX). The hydrogen donor is typically a metal hydride, such as a borohydride, formic acid, a formic acid alkali metal salt, and an alcohol, such as an alcohol having a hydrogen atom at a carbon atom that is a to the carbon atom to which the alcohol group is attached, such as iso-propanol.

A complex of formula (X) may be reacted with hydrogen (gaseous hydrogen) to yield (XX).

Similarly, a complex of formula (XI) may be converted to a complex of formula (XXI), where (XXI) is a compound of formula (XXIa) or (XXIb) having the structures shown below:

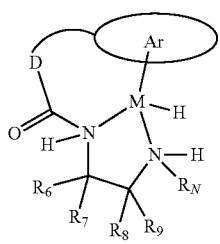

(XXIa)

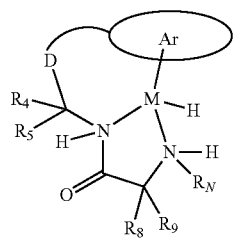

(XXIb)

where Ar, D, $R_4$, $R_5$, $R_6$, $R_7$, $R_8$, $R_9$, $R_N$, M and Hal have the same meanings as the complexes of formula (X).

The complex (XI) may be converted to (XXI) in the same manner as a complex (XX) is prepared from (X).

On completion of the reaction, the complexes made according to the present invention may be separated from the reaction mixture by any appropriate method which is dependent on the physical form of the product. In particular, solid complexes may be recovered by filtering, decanting or centrifuging. If purification is necessary, the complexes may be obtained in high purity by conventional methods.

The compound of formula (XX) or (XXI) may be used in a method of catalysis, such as a hydrogen reduction reaction.

A complex of formula (XX) or (XXI) may be formed in situ from a compound of formula (X) or (XI) during a hydrogen reduction reaction.

The methods described above may be performed under an inert atmosphere, such as an argon or nitrogen atmosphere.

Methods of Catalysis

In one aspect of the invention there is provided the use of a complex of formula (X) or formula (XI) as a catalyst, for example in a hydrogenation reaction or a transfer hydrogenation reaction. Such reactions may be broadly referred to as hydrogen reduction reactions.

In one embodiment, the method comprises the step of reacting a substrate comprising a carbon-heteroatom double bond in the presence of a complex of formula (X) or (XI). In one embodiment, the heteroatom may be O, S or N.

In alternative aspects of the invention, complexes of formula (XII), (XIII), (XX) or (XXI), and may be used in place of the complexes of formula (X) and (XI) in the reactions described below.

In one embodiment, the reaction is a hydrogenation reaction, and the method includes reacting the substrate with hydrogen in the presence of a complex of formula (X) or formula (XI).

In one embodiment, the reaction is a transfer hydrogenation, and the method includes reacting the substrate with a hydrogen donor in the in the presence of a complex of formula (X) or formula (XI).

The hydrogen donor is may be selected from formic acid, a formic acid alkali metal salt, and an alcohol, such as an alcohol having a hydrogen atom at a carbon atom that is a to the carbon atom to which the alcohol group is attached, such as iso-propanol. As used herein, a hydrogen donor is not gaseous hydrogen.

Examples of compounds containing a carbon-heteroatom double bond include ketone, aldehyde, imine and ketene compounds, amongst others.

The method may include the step of reducing a substrate, for example the hydrogenation of a carbonyl-containing substrate to yield the corresponding alcohol. In another embodiment, the method may include the step of hydrogenating an imino group to provide the corresponding amine.

A suitable substrate to be hydrogenated includes, but is not limited to, a carbonyl of formula (L):

(L)

wherein, $R_{50}$ and $R_{51}$ are each independently selected from the group consisting of hydrogen, an optionally substituted straight, branched or cyclic $C_{1-20}$ alkyl, an optionally substituted straight, branched or cyclic $C_{2-20}$ alkenyl, an optionally substituted $C_{2-20}$ alkynyl, an optionally substituted $C_{6-20}$ aryl, an optionally substituted straight, branched or cyclic $C_{1-20}$ heteroalkyl, an optionally substituted $C_{3-20}$ heteroaryl, —$NR_{60}R_{61}$, —$COR_{60}$, —$COOR_{60}$, —$CONR_{60}R_{61}$, an optionally substituted —$C_{1-20}$-alkyl-$COOR_{60}$, an optionally substituted —$C_{1-20}$-alkyl-$COR_{60}$, an optionally substituted —$C_{1-20}$-alkyl-$CONR_{60}R_{61}$, optionally substituted —$C_{2-20}$-alkynyl-$C_{6-20}$-aryl and optionally substituted —$C_{2-20}$-alkynyl-$C_{1-20}$-alkyl; or $R_{50}$ and $R_{51}$ are bound by an optionally substituted $C_{1-20}$ alkyl, an optionally substituted $C_{1-20}$ alkoxy or an optionally substituted $C_{2-20}$ alkenyl; or $R_{50}$ and $R_{51}$ are bound to form a 5, 6 or 7 membered ring by an optionally substituted —$(CH_2)_t$-(ortho-$C_{5-6}$-aryl)-$(CH_2)_u$— chain, an optionally substituted —$(CH_2)_t$-(ortho-$C_{5-6}$-aryl)-$L^Q$-$(CH_2)_u$— chain or an optionally substituted —$(CH_2)_t$-(ortho-$C_{5-6}$-heteroaryl)-$(CH_2)_u$— chain, wherein t is an integer selected from 0 or 1, u is an integer selected from 2, 3 or 4, -$L^Q$- is selected from the group consisting of —O—, —N— and —$SO_2$—, wherein the substituents are selected from the group consisting of one or more of straight, branched or cyclic $C_{1-20}$ alkyl, straight, branched or cyclic $C_{1-20}$ alkoxy, $C_{6-20}$ aryl, $C_{6-20}$ aryloxy, straight, branched or cyclic $C_{1-20}$ heteroalkyl, $C_{6-20}$ heteroaryl, straight or branched tri-$C_{1-20}$-alkylsilyl-, -Hal, —OH, —CN, —$NR_{60}R_{61}$, —$COR_{60}$, —$COOR_{60}$, —$CONR_{60}R_{61}$ and —$CF_3$, wherein $R_{60}$ and $R_{61}$ are independently selected from the group consisting of hydrogen, straight, branched or cyclic $C_{1-20}$ alkyl, straight, branched or cyclic $C_{1-20}$ alkoxy, $C_{6-20}$ aryl, $C_{6-20}$ aryloxy and —OH.

In one embodiment, $R_{50}$ and $R_{51}$ are not both hydrogen.

A suitable substrate to be hydrogenated includes, but is not limited to, a compound of formula (LI) or (LII):

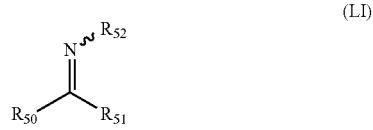

(LI)

-continued

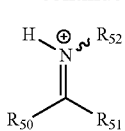
(LII)

wherein:

$R_{50}$ and $R_{51}$ are as described above with regard to the carbonyl of formula (L);

$R_{52}$ is selected from the group consisting of hydrogen, an optionally substituted straight, branched or cyclic $C_{1-20}$ alkyl, straight, branched or cyclic $C_{1-20}$ alkoxy, an optionally substituted straight, branched or cyclic $C_{2-20}$ alkenyl, an optionally substituted $C_{6-20}$ aryl, an optionally substituted $C_{6-20}$ aryloxy, an optionally substituted —$C_{1-20}$-alkyl-$C_{6-20}$-aryl, an optionally substituted straight, branched or cyclic $C_{1-20}$ heteroalkyl, an optionally substituted $C_{3-20}$ heteroaryl, —$NR_{70}R_{71}$, —$COR_{70}$, —$COOR_{70}$, —$CONR_{70}R_{71}$, an optionally substituted —$C_{1-20}$-alkyl-$COOR_{70}$, an optionally substituted —$C_{1-20}$-alkyl-$COR_{70}$, an optionally substituted —$C_{1-20}$-alkyl-$CONR_{70}R_{71}$, —$SOR_{70}$, —$SO_2R_{70}$, —$P(O)(R_{70})_2$, or $R_{52}$ and one of $R_{50}$ and $R_{51}$ are bound to form an optionally substituted $C_{1-20}$-heteroalkyl group, wherein the substituents are selected from the group consisting of one or more straight, branched or cyclic $C_{1-20}$ alkyl, straight, branched or cyclic $C_{1-20}$ alkoxy, $C_{6-20}$ aryl, $C_{6-20}$ aryloxy, straight, branched or cyclic $C_{1-20}$ heteroalkyl, $C_{6-20}$ heteroaryl, -Hal, —OH, —CN, —$NR_{70}R_{71}$, —$COOR_{70}$, —$CONR_{70}R_{71}$ or —$CF_3$, and wherein $R_{70}$ and $R_{71}$ are independently selected from the group consisting of hydrogen, straight, branched or cyclic $C_{1-20}$ alkyl, straight, branched or cyclic $C_{1-20}$ alkoxy, $C_{6-20}$ aryl, $C_{6-20}$ aryloxy, —OH, —C(O)—($C_{1-20}$-alkyl) and —C(O)O—($C_{1-20}$-alkyl).

When the substrate to be hydrogenated is a compound of formula (LII), any suitable anion may be present.

The reaction may be an asymmetric reduction reaction.

When $R_{50}$, $R_{51}$ and/or $R_{52}$ are different, the compounds of formulae (L), (LI) or (LII) are prochiral and the hydrogenation catalysed by the metal complex of formula (X) or (XI) may be enantioselective.

The enantiomeric excess may be greater than 80% ee. In certain embodiments, the enantiomeric excess is greater than 85% ee, in certain embodiments greater than 90% ee, in certain embodiments greater than 93% ee.

The reaction conditions for the reduction reactions are not particularly limited, and may be performed at the temperatures, pressures, concentrations that are appropriate to maximise the yield and stereoselectivity of the reaction, whilst minimising reaction time and reaction impurities.

Example reaction conditions for transfer hydrogenation reactions are described in WO 2012/026201 (for example, at pages 13-15), the contents of which are hereby incorporated by reference.

After the reduction reaction is deemed complete, the reaction mixture may be at least partially separated, for example to isolate the product, and/or to isolate the complex. In a stereoselective reaction the product may be isolated from undesired stereoisomers.

The complexes of the invention may be separated from the reaction mixture by precipitation, for example following the addition of a polar solvent to the reaction mixture or following the concentration of the reaction mixture.

The methods described above may be performed under an inert atmosphere, such as an argon or nitrogen atmosphere.

Substituent Groups

The point of attachment of a moiety or substituent is represented by "—". For example, —OH is attached through the oxygen atom.

Alkyl refers to a straight-chain, branched or cyclic saturated hydrocarbon group. In certain embodiments, the alkyl group may have from 1-20 carbon atoms, in certain embodiments from 1-15 carbon atoms, in certain embodiments, 1-10 carbon atoms, or 1-6 carbon atoms. The number of carbon atoms is appropriate to the group e.g. a cycloalkyl group must have at least 3 carbon atoms to form a ring. The alkyl group may be unsubstituted. Alternatively, the alkyl group may be substituted. Unless otherwise specified, the alkyl group may be attached at any suitable carbon atom and, if substituted, may be substituted at any suitable atom. Typical alkyl groups include but are not limited to methyl, ethyl, n-propyl, iso-propyl, cyclopropyl, n-butyl, iso-butyl, sec-butyl, tert-butyl, cyclobutyl, n-pentyl, cyclopentyl, n-hexyl, cyclohexyl and the like. A cycloalkyl group may have two or more fused rings (bridge structures), such as a decalinyl group or a bicyclo[2.2.1]heptyl group. In one embodiment, alkyl is an acyclic group.

Alkoxy refers to a —O-alkyl group wherein the alkyl group is as described above.

Cycloalkadienyl refers to a cyclic unsaturated hydrocarbon group having two unsaturated carbon-carbon bonds (two carbon-carbon double bonds). The unsaturated bonds may be conjugated or may be unconjugated. In certain embodiments, the cycloalkadienyl group has 5-6 carbon atoms. The cycloalkadienyl group may be unsubstituted. Alternatively, the cycloalkyldienyl group may be substituted. Unless otherwise specified, the alkyl group may be attached at any suitable carbon atom and, if substituted, may be substituted at any suitable atom. A typical cycloalkadienyl group is cyclohexadienyl, such as cyclohexa-1,4-dienyl and cyclohexa-1,3-dienyl.

Alkenyl refers to a straight-chain, branched or cyclic unsaturated hydrocarbon group having at least one carbon-carbon double bond. The group may be in either the cis- or trans-configuration around each double bond. In certain embodiments, the alkenyl group can have from 2-20 carbon atoms, in certain embodiments from 2-15 carbon atoms, in certain embodiments, 2-10 carbon atoms. The number of carbon atoms is appropriate to the group e.g. a cyclic group having at least one carbon-carbon double bond must have a sufficient number of carbon atoms in order for the cyclic group to be formed. The alkenyl group may be unsubstituted. Alternatively, the alkenyl group may be substituted. Unless otherwise specified, the alkenyl group may be attached at any suitable carbon atom and, if substituted, may be substituted at any suitable atom. Examples of alkenyl groups include but are not limited to ethenyl (vinyl), 2-propenyl (allyl), 1-methylethenyl, 2-butenyl, 3-butenyl, cyclobut-1,3-dienyl and the like.

Alkynyl refers to a straight-chain, branched or cyclic unsaturated hydrocarbon group having at least one carbon-carbon triple bond. In certain embodiments, the alkynyl group can have from 2-20 carbon atoms, in certain embodiments from 2-15 carbon atoms, in certain embodiments, 2-8 carbon atoms. The number of carbon atoms is appropriate to the group e.g. a cyclic group having at least one carbon-carbon triple bond must have a sufficient number of carbon atoms in order for the cyclic group to be formed. The alkynyl group may be unsubstituted. Alternatively, the alkynyl group may be substituted. Unless otherwise specified, the alkynyl group may be attached at any suitable carbon atom and, if substituted, may be substituted at any suitable atom. Examples of alkynyl groups include, but are not limited to, ethynyl, prop-1-ynyl, prop-2-ynyl, 1-methylprop-2-ynyl, but-1-ynyl, but-2-ynyl, but-3-ynyl and the like.

Aryl refers to an aromatic carbocyclic group. The aryl group may have a single ring or multiple condensed rings. In certain embodiments, the aryl group can have from 6-20 carbon atoms, in certain embodiments from 6-15 carbon atoms, in certain embodiments, 6-10 carbon atoms. The aryl group may be unsubstituted or substituted. Unless otherwise specified, the aryl group may be attached at any suitable carbon atom and, if substituted, may be substituted at any suitable atom. Examples of aryl groups include, but are not limited to, phenyl, naphthyl, anthracenyl and the like.

It is noted that the present case relates to complexes having an aryl group, Ar, that is connected to a metal atom, M. For example, the present case describes complexes having $\eta^5$ or $\eta^6$ aryl group ligands. Thus where reference is made to aryl within the group Ar, the number of carbon atoms may be from 5-20 carbon atoms, in certain embodiments from 5-15 carbon atoms, in certain embodiments, 5-10 carbon atoms.

Aryloxy refers to an —O-aryl group wherein the aryl group is as described above.

Hal refers to a halogen and may be selected from the group consisting of fluorine, chlorine, bromine and iodine.

Heteroalkyl refers to a straight-chain, branched or cyclic saturated hydrocarbon group wherein one or more carbon atoms are independently replaced with one or more heteroatoms (e.g. nitrogen, oxygen, phosphorus and/or sulfur atoms). In certain embodiments, the heteroalkyl group may have from 1-20 carbon atoms, in certain embodiments from 1-15 carbon atoms, in certain embodiments, 1-10 carbon atoms. The number of carbon atoms is appropriate to the group e.g. a heterocycloalkyl group must have a sufficient number of carbon atoms together with the heteroatom to form a ring. The heteroalkyl group may be unsubstituted. Alternatively, the heteroalkyl group may be substituted. Unless otherwise specified, the alkyl group may be attached at any suitable atom and, if substituted, may be substituted at any suitable atom. Examples of heteroalkyl groups include, but are not limited to, ethers, thioethers, primary amines, secondary amine, tertiary amines, epoxide, morpholinyl, piperadinyl, piperazinyl, thirranyl and the like.

Heteroaryl refers to an aromatic carbocyclic group wherein one or more carbon atoms are independently replaced with one or more heteroatoms (e.g. nitrogen, oxygen, phosphorus and/or sulfur atoms). In certain embodiments, the heteroaryl group may have from 3-20 carbon atoms, in certain embodiments from 3-15 carbon atoms, in certain embodiments, 3-10 carbon atoms, in certain embodiments 5-10 carbon atoms, and in certain embodiments 5-6 carbon atoms. A reference to a $C_{3-20}$ heteroaryl group is a reference to an aromatic cyclic group having one or more (e.g. 1, 2 or 3) heteroatoms and from 3 to 20 carbon atoms in the aromatic ring. The heteroaryl group may be unsubstituted or substituted. Unless otherwise specified, the heteroaryl group may be attached at any suitable atom and, if substituted, may be substituted at any suitable atom. Examples of heteroaryl groups include, but are not limited to, furanyl, indolyl, oxazolyl, pyrrolyl, N-methyl-pyrrolyl, pyridinyl, pyrimidinyl, pyridazinyl, thiazolyl, thiophenyl and the like.

Substituted refers to a group in which one or more hydrogen atoms are each independently replaced with substituents (e.g. 1, 2, 3, 4, 5 or more) which may be the same or different.

Examples of substituents include but are not limited to -halo, —C(halo)$_3$, —R$^a$, =O, =S, —O—R$^a$, —S—R$^a$, —NR$^a$R$^b$, —CN, —NO$_2$, —C(O)—R$^a$, —COOR$^a$, —C(S)—R$^a$, —C(S)OR$^a$, —S(O)$_2$OH, —S(O)$_2$—R$^a$, —S(O)$_2$NR$^a$R$^b$, —O—S(O)—R$^a$ and —CONR$^a$R$^b$, such as -halo, —C(halo)$_3$ (e.g. —CF$_3$), —R$^a$, —O—R$^a$, —NR$^a$R$^b$, —CN, or —NO$_2$. R$^a$ and R$^b$ are independently selected from the groups consisting of H, alkyl, aryl, arylalkyl, heteroalkyl, heteroaryl, or R$^a$ and R$^b$ together with the atom to which they are attached form a heterocycloalkyl group. R$^a$ and R$^b$ may be unsubstituted or further substituted as defined herein. In one embodiment, a group that is optionally substituted may be unsubstituted.

Example optional substituent groups include straight, branched or cyclic $C_{1-10}$ alkyl, straight, branched or cyclic $C_{1-10}$ alkoxy, $C_{6-10}$ aryl and $C_{6-20}$ aryloxy, —OH, —CN, —NR$_{20}$R$_{21}$, —COOR$_{20}$, —CONR$_{20}$R$_{21}$ and —CF$_3$.

In one embodiment, an alkyl group is not further substituted with an alkyl group.

Other Preferences

Each and every compatible combination of the embodiments described above is explicitly disclosed herein, as if each and every combination was individually and explicitly recited.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of the following non-limiting examples.

Abbreviations

DCM: dichloromethane

DMF: dimethylformamide

DMSO: dimethylsulfoxide

Dpen: 1,2-diphenylethylendiamine

EDC: 1-ethyl-3-(3-dimethylaminopropyl)carbodiimide

EN: 1,2-ethylendiamine

HOBt: N-hydroxybenzotriazole

Me-THF: 2-methyltetrahydrofuran

MTBE: methyl tert-butyl ether r.t.: room temperature

Sat.: saturated t-BuOH: tert-butyl alcohol

THF: tetrahydrofuran

Ts-: 4-methylphenylsulfonyl, p-toluenesulfonyl

Tris-: 2,4,6-triisopropyl-benzenesulfonyl

EXAMPLES

All reactions were carried out under an inert atmosphere, such as an argon or nitrogen atmosphere.
Preparation of Ligands and Complexes Example 1: 3-Cyclohexa-1,4-dienyl-propionic Acid

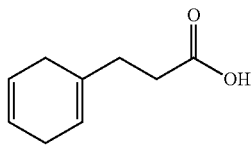 [SMILES: O=C(O)CCC1=CCC=CC1]

3-Phenylpropionic acid (3 g, 20 mmol) and t-BuOH (10.56 g) were placed to 250 mL round bottom flask equipped with magnetic stirrer and dry ice cooling finger. Flask was placed to Acetone/dry ice bath and 70 mL of ammonia were condensed into the flask. Lithium (1.23 g, 176 mmol, 8.8 eq.) was gradually added to the reaction flask. Reaction mixture was stirred at −78° C. for 5 hours and sat. NH$_4$Cl (50 mL) was added to quench the reaction. Cooling was removed and the ammonia was left to evaporate. The residue was dissolved in water (100 mL) and pH was adjusted to 2-3 using 10% HCl. Product was extracted with t-BuOMe (3×50 mL), combined phases washed with brine (50 mL) dried over magnesium sulfate and solvent was evaporated to give the title compound as white solid (3.17 g, quant, 7% of starting material still present). δH (400 MHz, CDCl$_3$) 5.65-5.60 (m, 2H, CH═CH), 5.40-5.38 (1H, m, C═CH), 2.65-2.49 (m, 4H, CH$_2$), 2.46-2.39 (2H, m, CH$_2$), 2.27-2.19 (2H, m, CH$_2$); δC (100 MHz, CDCl$_3$) 179.7, 133.0, 124.2, 124.0, 119.2, 32.2, 32.0, 29.0, 26.7. Compound reported in literature (*J. Am. Chem. Soc.* 1983, 105, 2364-2368) without spectroscopic data.

Example 2: 4-(cyclohexa-1,4-dien-1-yl)butanoic Acid

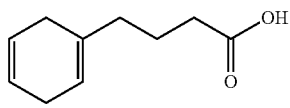 [SMILES: O=C(O)CCCC1=CCC=CC1]

4-Phenylbutyric acid (3.28 g, 20 mmol) and t-BuOH (10.56 g) were placed to 250 mL round bottom flask equipped with magnetic stirrer and dry ice cooling finger. Flask was placed to Acetone/dry ice bath and 70 mL of ammonia were condensed into the flask. Lithium (1.23 g, 176 mmol, 8.8 eq.) was gradually added to the reaction flask. Reaction mixture was stirred at −78° C. for 5 hours and sat. NH$_4$Cl (50 mL) was added to quench the reaction. Cooling was removed and the ammonia was left to evaporate. The residue was dissolved in water (100 mL) and pH was adjusted to 2-3 using 10% HCl. Product was extracted with t-BuOMe (3×50 mL), combined phases washed with brine (50 mL) dried over magnesium sulfate and solvent was evaporated to give the title compound as white solid (3.5 g, quant.). δH (400 MHz, CDCl$_3$) 5.78-5.65 (m, 2H, CH═CH), 5.50-5.43 (1H, m, C═CH), 2.76-2.55 (m, 4H, CH$_2$), 2.43-2.32 (2H, m, CH$_2$), 2.10-1.97 (2H, m, CH$_2$), 1.86-1.73 (2H, m, CH$_2$); δC (100 MHz, CDCl$_3$) 179.8, 133.7, 124.23, 124.19, 119.4, 36.6, 33.4, 28.7, 26.7, 22.2.

Spectroscopic data were consistent with literature values (*Eur. J. Inorg. Chem.* 2003, 1873-1882).

Example 3: 3-(cyclohexa-1,4-dien-1-yl)propan-1-amine

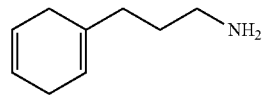

3-Phenylpropyl amine (2.76 g, 20 mmol) and EtOH (30 mL) were placed to 250 mL round bottom flask equipped with magnetic stirrer and dry ice cooling finger. Flask was placed to Acetone/dry ice bath (−78° C.) and ammonia (ca. 70 mL) was condensed into the flask. Lithium (1.23 g, 176 mmol, 8.8 eq.) was gradually added to the reaction mixture and mixture turned deep blue. After the blue colour disappeared, additional lithium was added (0.4 g, 57 mmol) flask. Reaction mixture was stirred at −78° C. for additional 1 hour during which the dark blue colour disappeared again. Sat. NH$_4$Cl (50 mL) was added to quench the reaction. The cooling was removed and ammonia was allowed to evaporate. The remaining residue was dissolved in water (100 mL) and extracted with DCM (3×50 mL) Combined organic phases were washed with brine (50 mL) dried over magnesium sulphate and solvent was evaporated to give the title compound as colourless liquid (2.7 g, quant.). δH (400 MHz, CDCl$_3$) 5.68-5.57 (m, 2H, CH═CH), 5.41-5.31 (1H, m, C═CH), 2.67-2.57 (m, 4H, CH$_2$), 2.57-2.48 (2H, m, CH$_2$), 1.97-1.86 (2H, m, CH$_2$), 1.56-1.44 (2H, m, CH$_2$), 1.25 (bs, 2H, NH$_2$); δC (100 MHz, CDCl$_3$) 134.6, 124.3, 118.5, 42.0, 34.8, 31.4, 28.9, 26.8. Compound reported in *J. Med. Chem.* 1989 32 1259, but sufficient spectroscopic data were not provided.

Example 4: 4-(cyclohexa-1,4-dien-1-yl)butane-1-amine

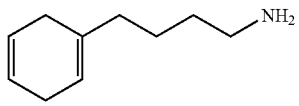 [SMILES: NCCCCC1=CCC=CC1]

4-Phenylbutyl amine (2.98 g, 20 mmol) and t-BuOH (10.56 g) were placed to 250 mL round bottom flask equipped with magnetic stirrer and dry ice cooling finger. Flask was placed to Acetone/dry ice bath (−78° C.) and ammonia (ca 70 mL) was condensed into the flask. Lithium (1.23 g, 176 mmol, 8.8 eq.) was gradually added to the reaction mixture and mixture turned deep blue. Cooling was removed from the flask and the reaction mixture was stirred at refluxing temperature of ammonia for 5 h (dry ice condenser was connected to the flask). Sat. NH$_4$Cl (50 mL) was added to quench the reaction and the ammonia was allowed to evaporate. The remaining residue was dissolved in water (100 mL) and extracted with DCM (3×50 mL) Combined organic phases were washed with brine (50 mL) dried over magnesium sulfate and solvent was evaporated to give the title compound as colourless liquid (3 g, quant.). δH (400 MHz, CDCl$_3$) 5.68-5.59 (m, 2H, CH═CH), 5.39-5.31 (1H, m, C═CH), 2.65-2.57 (m, 4H, CH$_2$), 2.57-2.46 (2H, m, CH$_2$), 1.96-1.85 (2H, m, CH$_2$), 1.45-1.26 (6H, m, CH$_2$, NH$_2$.

Compound reported in *J. Med. Chem.* 1989 32 1259, but sufficient spectroscopic data were not provided.

Example 5: N-(2-Aminoethyl)-2,4,6-triisopropyl Benzene Sulfonamide, Tris-EN

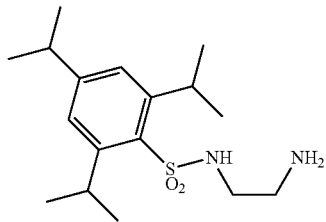 [SMILES: CC(C)c1cc(C(C)C)c(S(=O)(=O)NCCN)c(C(C)C)c1]

A solution of trisisopropylbenzenesulfonyl chloride (10.0 g, 33.8 mmol) in DCM (100 mL) was slowly added dropwise at room temperature over ~10 min to a stirred solution of ethylenediamine (19.8 g, 22.0 mL, 330 mmol) in DCM (100 mL). The resulting mixture was stirred for 15 min (if the reaction is left too long di-addition to ethylenediamine is observed). The mixture was then washed twice with water (100 mL) and dried over $Na_2SO_4$. The solvent was removed in vacuo to yield the desired product (9.12 g, 28.0 mmol, 83%), which was used directly in the next step without further purification. Mp: 118-120° C.; $\delta_H$ (400 MHz, $CDCl_3$) 7.17 (2H, s, ArH), 4.15-4.22 (2H, m, o-CH(Me)$_2$), 2.98-3.01 (2H, m, $CH_2NH$), 2.87-2.93 (1H, m, p-CH(Me)$_2$), 2.82-2.85 (2H, m, $CH_2NH_2$), 1.25-1.28 (18H, m, CH(CH$_3$)$_2$), the NH protons were not observed; $\delta_C$ (100 MHz, $CDCl_3$) 152.6 (2C), 150.3, 132.1, 123.8 (2C), 45.0, 40.9, 34.1, 29.6 (2C), 24.9 (4C), 23.6 (2C); m/z (ESI) 327.1 (M+H)$^+$, 100). Spectroscopic data in accordance with the literature: J. Tan, W. Tang, Y. Sun, Z. Jiang, F. Chen, L. Xu, Q. Fan and J. Xiao, *Tetrahedron* 2011, 67, 6206-6213.

Example 6: Methyl N-[2,4,6-tri(propan-2-yl)phenyl]sulfonyl-glycinate

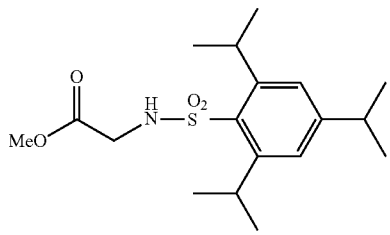 [SMILES: COC(=O)CNS(=O)(=O)c1c(C(C)C)cc(C(C)C)cc1C(C)C]

Glycine methyl ester (10.4 g, 82.5 mmol) was added to a flask to which methanol (100 mL) was added. Then triethylamine (16.7 g, 23 mL, 165 mmol) was added to the flask, this was left to stir for 10 mins. After which time 2,4,6-tri-iso-propylbenzene sulfonyl chloride (5.0 g, 16.5 mmol) was added in one portion. This was left to stir overnight at room temperature to yield the glycinate product (2.96 g, 8.34 mmol, 51%) as an off-white solid. mp: 120-122° C.; found (EI): [M+Na]$^+$, 378.1706. $C_{18}H_{29}NNaO_4S$ requires: 378.1710. $\delta_H$ (400 MHz, $CDCl_3$) 7.17 (2H, s, TrisArH), 5.00 (1H, t, J=5.0, NH), 4.13 (2H, spt, J=6.7, o-iPr(CH)), 3.79 (2H, d, J=5.5, $CH_2$), 3.69 (3H, s, $OCH_3$), 2.90 (1H, spt, J=6.9, p-iPr(CH)), 1.15-1.33 (18H, m, iPr(CH$_3$)); $\delta_C$ (100 MHz, $CDCl_3$) 169.4, 153.1, 150.5 (2C), 131.7, 123.9 (C2), 52.6, 43.8, 34.2, 29.8 (C2), 24.9 (C4), 23.6 (C2); m/z (ESI): 354.1 ([M−H]$^+$, 100%).

Example 7: N-[2,4,6-tri(propan-2-yl)phenyl]sulfonyl-glycine

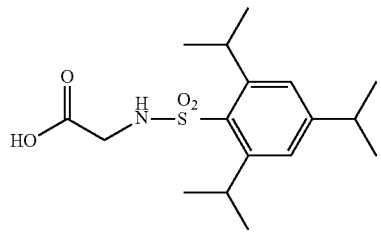 [SMILES: CC(C)c1cc(C(C)C)c(S(=O)(=O)NCC(=O)O)c(C(C)C)c1]

To a stirred solution of methyl N-[2,4,6-tri(propan-2-yl)phenyl]sulfonyl-glycinate (1.00 g, 2.81 mmol) in methanol/water (1:2 v/v, 24 mL) was added potassium hydroxide (1.57 g, 28.0 mmol) in methanol/water (1:2 v/v, 12 mL). The reaction was heated to 70° C. under reflux. After stirring for 2 h, the reaction was mixture cooled to 0° C. and acidified using 2M HCl aq. solution (~10 mL) to pH 7. The resulting mixture was washed with ethyl acetate (3×100 mL). The combined organics was washed with brine (3×50 mL) and dried with $Na_2SO_4$. The solvent was removed under vacuum to yield a white solid (885 mg, 2.6 mmol, 93%). Mp: 141-143□C; (found (ESI): [M+Na]$^+$, 364.1556. $C_{17}H_{27}NNaO_4S$ requires: 364.1558); $\delta_H$(400 MHz, $CDCl_3$) 10.33 (1H, br. s, OH), 7.17 (2H, s, TrisArH), 5.13 (1H, t, J=5.5, $CH_2$), 4.10 (2H, spt, J=6.0, o-iPr(CH)), 3.84 (2H, d, J=5.5, $CH_2$), 2.90 (1H, spt, J=6.0, p-iPr (CH)), 1.26 (12H, d, J=7.0, o-iPr(CH$_3$)), 1.25 (6H, d, J=8.0, p-iPr(CH$_3$)); $\delta_C$ (100 MHz, $CDCl_3$) 174.1, 153.3, 150.5 (2C), 131.4, 124.0 (2C), 43.6, 34.2, 29.8 (2C), 24.8 (4C), 23.5 (2C); m/z (ESI): 340.1 ([M−H]$^+$, 100%).

Scheme 1: Synthesis of C3-[Ts-Dpen-teth RuCl].

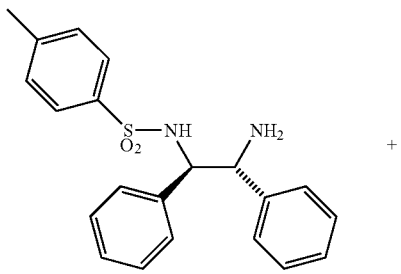

+

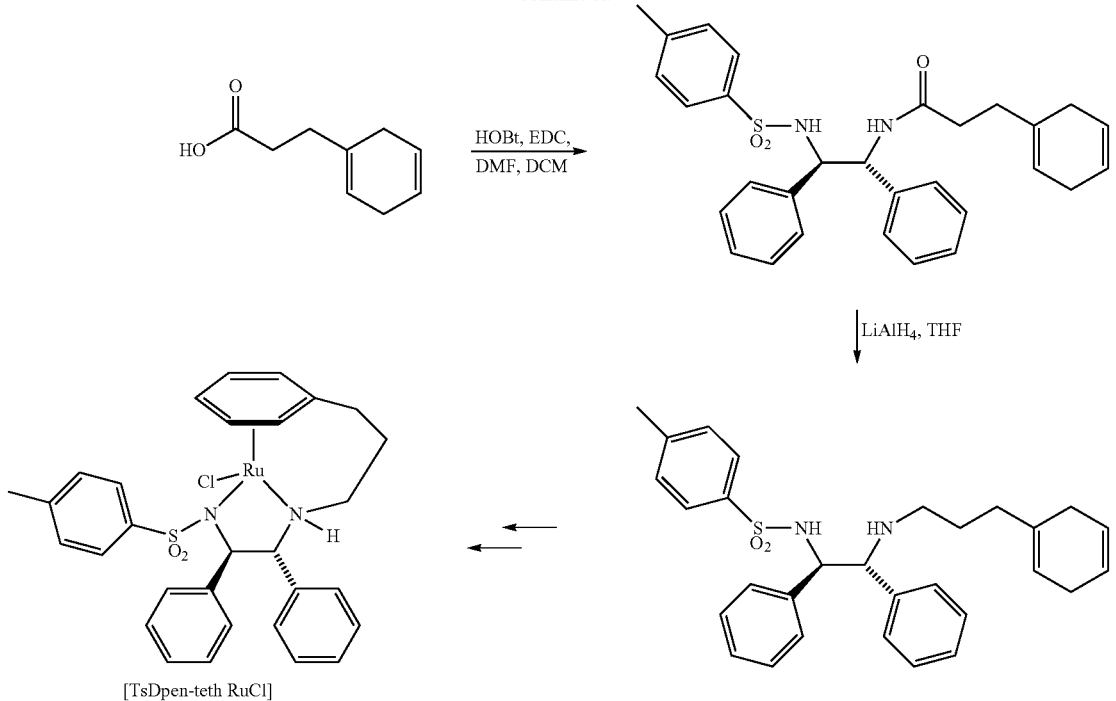

Example 8: 3-Cyclohexa-1,4-dienyl-N-(1R,2R)-[1,2-diphenyl-2-(toluene-4-sulfonylamino)-ethyl]-propionamide

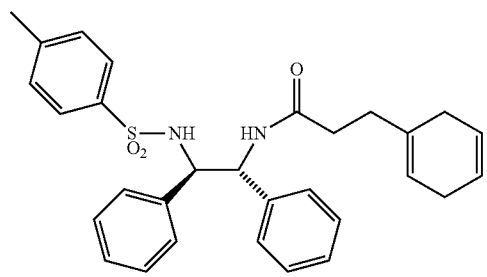 [SMILES: Cc1ccc(S(=O)(=O)N[C@H](c2ccccc2)[C@H](NC(=O)CCC2=CCC=CC2)c2ccccc2)cc1]

To a round bottom flask, was added 3-cyclohexa-1,4-dienyl-propionic acid (200 mg, 1.32 mmol), HOBt (195 mg, 1.44 mmol) and (R,R)-TsDPEN (513 mg, 1.40 mmol) which were dissolved in anhydrous DCM (4 mL) and DMF (4 mL). The solution was cooled to 0° C., then EDC (242 mg, 1.56 mmol) was added. The temperature was maintained for 1 h. The reaction was then allowed to warm to rt and left overnight. Water (50 mL) was added and the resulting mixture was extracted using EtOAc (3×50 mL). The combined organic extracts were washed with water (3×100 mL) and brine (3×100 mL), and then dried with $Na_2SO_3$ and concentrated to give an off white-solid (613 mg, 1.23 mmol, 93%). Mp: 184-186° C. (dec.); $[\alpha]_D^{26}$ +10.8 (c 0.53 in $CHCl_3$); found (EI): $[M+Na]^+$, 521.1855. $C_{30}H_3N_2NaO_3S$ requires M, 521.1869; $\delta_H$ (400 MHz, $CDCl_3$) 7.42 (2H, d, J=8.5, TsArH), 7.13-7.19 (4H, m, ArH), 6.93 (2H, d, J=8.5, TsArH), 6.88-6.89 (6H, m, ArH), 5.84 (2H, br. s, CH=CH), 5.32-5.36 (2H, m, C=CH and CH(Ph)), 4.66 (1H, t, J=9.3, CH(Ph)), 2.57-2.61 (2H, m, $CH_2$), 2.47-2.52 (2H, m, $CH_2$), 2.34-2.40 (2H, m, $CH_2$), 2.27-2.32 (2H, m, $CH_2$), 2.22 (3H, s, $TsCH_3$); $\delta_C$ (100 MHz, $CDCl_3$) 173.9, 142.6, 139.2, 138.0, 137.8, 133.5, 129.2 (2C), 128.5, 128.4, 128.3 (2C), 128.0 (2C), 127.6 (2C), 127.3, 126.8 (2C), 124.2, 124.1 (2C), 119.2, 63.0, 58.8, 34.6, 32.9, 29.0, 26.8, 21.4; m/z (ESI) 521.1 ($[M+Na]^+$, 100%).

Example 9: N-(1R,2R)-[2-(3-Cyclohexa-1,4-dienyl-propylamino)-1,2-diphenyl-ethyl]-4-methyl-benzene Sulphonamide

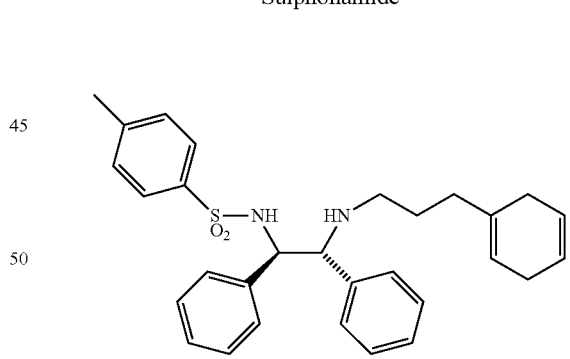

To a solution of 2 M $LiAlH_4$ in THF (0.80 mL, 1.6 mmol) was added 3-cyclohexa-1,4-dienyl-N-[1,2-diphenyl-2-(toluene-4-sulfonylamino)-ethyl]-propionamide (200 mg, 0.40 mmol) in dry THF (4 mL). The mixture was then heated to reflux (70° C.) and left overnight. The reaction was cooled to room temperature, and water (1 mL) was added together with 10% NaOH solution (1 mL). The mixture was then filtered through a plug of celite washing the plug DCM (50 mL). The aqueous layer was then extracted using DCM (3×50 mL) and the combined organic extracts were dried with $Na_2SO_3$. The solution was then concentrated to give a white solid (150 mg, 0.31 mmol, 77%). Spectroscopic data is in agreement with literature: a) A. M. Hayes, D. J. Morris, G. J. Clarkson and M. Wills, *J. Am. Chem. Soc.,* 2005, 127, 7318-7319. B) K. E. Jolley, A. Zanotti-Gerosa, F. Hancock, A. Dyke, D. M. Grainger, J. A. Medlock, H. G. Nedden, J. J. M. Le Paih, S. J. Roseblade, A. Seger, V. Sivakumar, I. Prokes, D. J. Morris and M. Wills, *Adv. Synth. Catal.,* 2012, 354, 2545-2555.

The subsequent synthetic steps to prepare [Ts-Dpen-teth RuCl] may be carried out as described in the literature: K. E. Jolley, A. Zanotti-Gerosa, F. Hancock, A. Dyke, D. M. Grainger, J. A. Medlock, H. G. Nedden, J. J. M. Le Paih, S. J. Roseblade, A. Seger, V. Sivakumar, I. Prokes, D. J. Morris and M. Wills, *Adv. Synth. Catal.,* 2012, 354, 2545-2555.

$[\alpha]_D^{26}$ +15.6 (c 0.59 in CHCl$_3$); found (EI): [M+Na]$^+$ 521.1872. requires: C$_{30}$H$_{30}$N$_2$NaO$_3$S 521.1869; $\delta_H$ (400 MHz, CDCl$_3$) 7.44 (2H, d, J=8.0, TsArH), 7.12-7.23 (9H, m, ArH), 7.01 (2H, d, J=9.0, TsArH), 6.90-6.96 (4H, m, ArH), 6.79-6.81 (2H, m, ArH), 6.62 (2H, t, J=9.0, NH), 5.22 (1H, dd, J=10.0 and 8.0, CH(Ph)), 4.56 (1H, t, J=8.0, CH(Ph)), 2.98 (2H, t, J=7.5, CH$_2$), 2.49-2.65 (2H, m, CH$_2$), 2.27 (3H, s, CH$_3$); $\delta_C$ (100 MHz, CDCl$_3$) 173.6, 142.9, 140.6, 138.3, 137.9, 137.7, 129.2 (2C), 128.6 (2C), 128.5 (2C), 128.4 (2C), 128.1 2C), 127.8 (2C), 127.5 (3C), 126.8 (2C), 126.2, 63.3, 58.8, 38.3, 31.5, 21.4; m/z (ESI): 521.1 ([M+Na]$^+$, 100%).

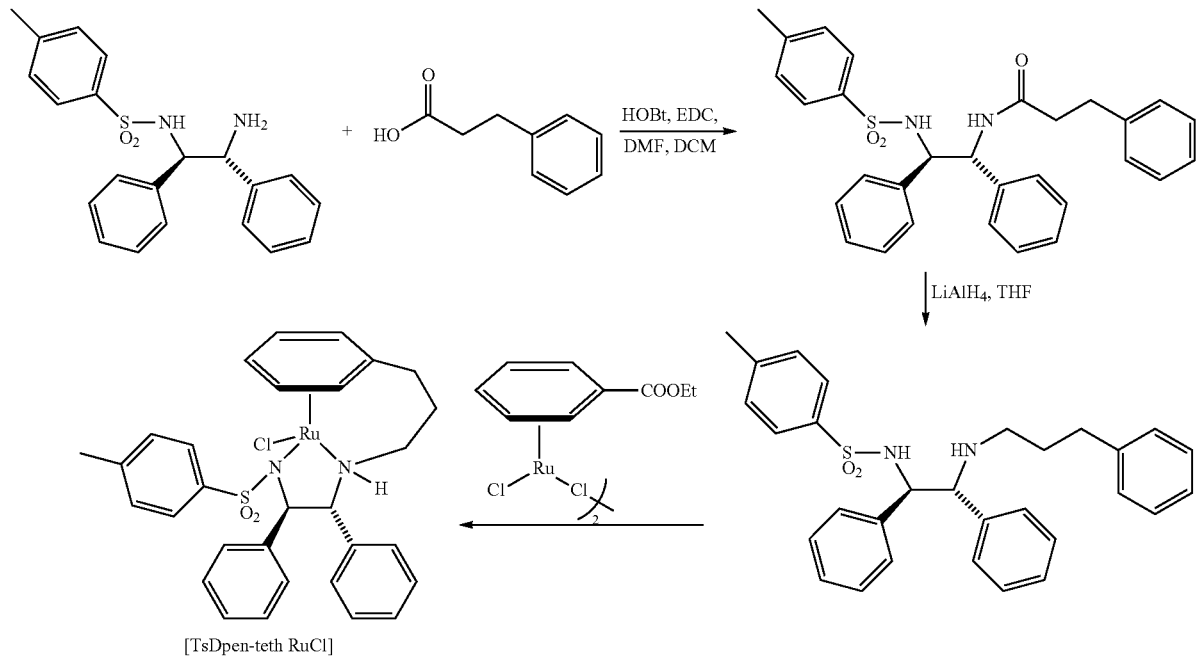

Scheme 2: Alternative Synthesis of C3-[Ts-Dpen-teth-RuCl]

[TsDpen-teth RuCl]

Example 10: N-(1R,2R)-[1,2-Diphenyl-2-(toluene-4-sulfonylamino)-ethyl]-3-phenyl-propionamide Example 11: N-(1R,2R)-[2-(3-phenyl-propylamino)-1,2-diphenyl-ethyl]-4-methyl-benzene Sulphonamide

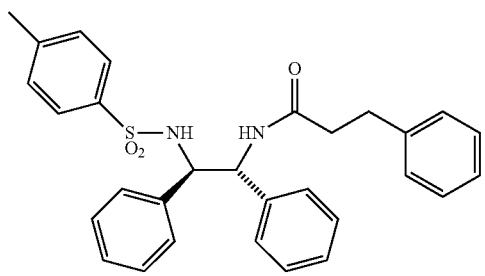 [SMILES: Cc1ccc(S(=O)(=O)N[C@H](c2ccccc2)[C@H](NC(=O)CCc2ccccc2)c2ccccc2)cc1]

The preparation uses the method described in example 8, using 3-phenyl-propanoic acid (1.00 g, 6.66 mmol), TsD-PEN (2.68 g, 7.32 mmol), HOBt (0.99 g, 7.33 mmol) and EDC (1.23 g, 7.93 mmol) in anhydrous DCM (20 mL) and anhydrous DMF (20 mL). The amide was obtained as an off-white solid (3.07 g, 6.16 mmol, 93%); mp: 195-197° C.;

Prepared using the method described in example 9: N-(1R,2R)-[2-(3-phenyl-propylamido)-1,2-diphenyl-ethyl]-4-methyl benzenesulfonamide (1.00 g, 2.01 mmol) and 2M LiAlH$_4$ in THF (4 mL, 8.0 mmol) in anhydrous THF (20 mL). The product was obtained as an off-white solid (644 mg, 1.33 mmol, 66%). Spectroscopic data is in accordance with literature: a) J. E. D Martins, D. J.; Morris, M. Wills, *Tetrahedron Lett.* 2009, 50, 688-692.

The subsequent synthetic steps to prepare [Ts-Dpen-teth RuCl] may be carried out as described in the literature: R. Soni, K. E. Jolley, M. Wills, *Organic Lett.* 2013, 15, 5110-5113.

and the residue was diluted with EtOAc (40 mL), washed with 10% Na₂CO₃ (50 mL), 0.1 M HCl (50 mL), brine (50 mL) and dried over magnesium sulphate. The solvent was removed under reduced pressure to give the amide as white solid (6.19 g, quant.). δH (400 MHz, CDCl₃) 7.10-7.05 (3H, m, ArH), 6.95-6.90 (5H, m, ArH), 6.86 (3H, t, J=7.3 Hz,

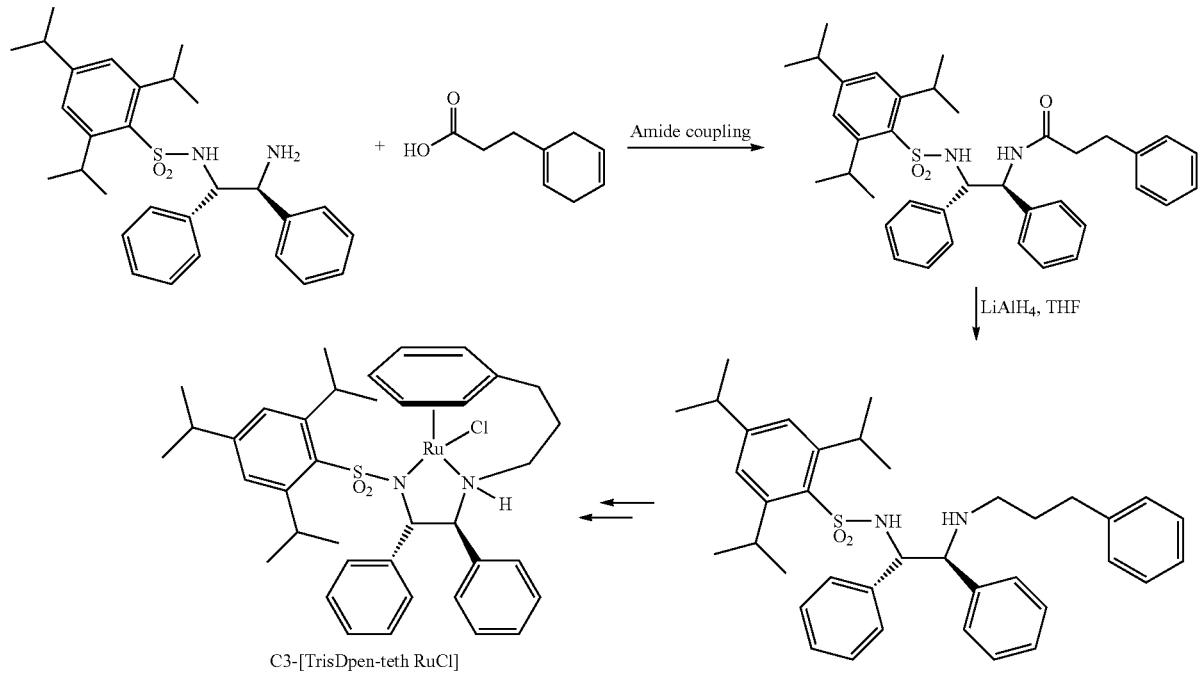

Scheme 3: Synthesis of C3-[Tris-Dpen-teth-RuCl]

C3-[TrisDpen-teth RuCl]

Example 12: 3-Cyclohexa-1,4-dienyl-N-(1S,2S)-[1,2-diphenyl-2-(2,4,6-triisopropyl-benzene sulfonylamino)-ethyl]-propionamide

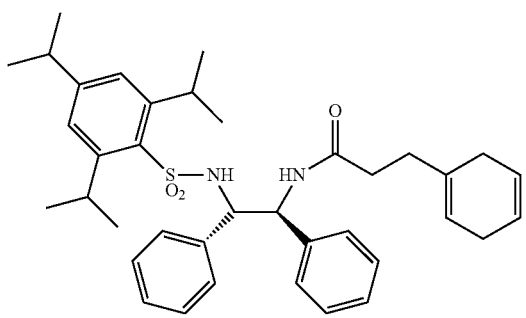

3-Cyclohexa-1,4-dienyl-propionic acid (1.52 g, 10.00 mmol) was dissolved in dry THF (30 mL) and N-methylmorpholine (1.01 mL, 10.00 mmol) was added. The reaction mixture was cooled down to −15° C. and a solution of i-butyl chloroformate (1.36 g, 1.30 mL, 10.00 mmol) in THF (5 mL) was added dropwise over a period of 15 min. After addition was completed, the mixture was stirred at −15° C. for another 15 min and (S,S)-TrisDPEN (10.00 mmol, 1 eq.) was added at once. The cooling was then removed and the reaction mixture was allowed to warm up to r.t. and stirred overnight. The solvent was removed under reduced pressure ArH), 6.62-6.57 (2H, m, ArH), 5.87 (1H, d, J=7.7 Hz, NH), 5.65-5.60 (2H, m, CH═CH), 5.43-5.39 (1H, m, C═CH), 5.17 (1H, dd, J, =11, J₂=7.6 Hz, CH(Ph)), 4.40 (1H, dd, J, =11, J₂=7.6 Hz, CH(Ph)), 3.98-3.85 (2H, m, CH(CH₃)₂), 2.80-2.70 (1H, m, CH(CH₃)₂), 2.64-2.50 (4H, m, CH₂), 2.49-2.24 (4H, m, CH₂); 1.1 (12H, dd, J, =6.3 Hz, J₂=7.2 Hz, CH(CH₃)₂)) 0.9 (6H, J=6.7 Hz, CH(CH₃)₂).

Example 13: N-(1S,2S)-[2-(3-Cyclohexa-1,4-dienyl-propylamino)-1,2-diphenyl-ethyl]-2,4,6-triisopropyl-benzene Sulfonamide

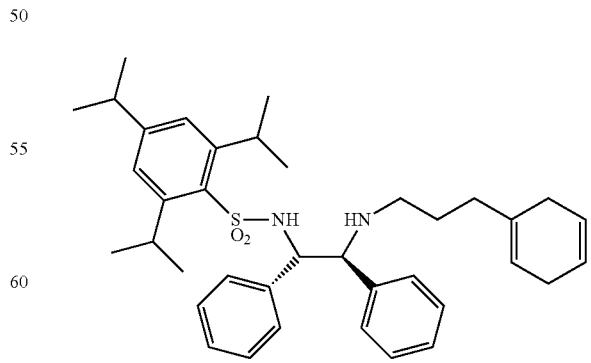

3-Cyclohexa-1,4-dienyl-N-[1,2-diphenyl-2-(2,4,6-triisopropyl-benzenesulfonylamino)-ethyl]-propionamide (6.19 g, 10.00 mmol) was dissolved in dry THF (100 mL) and LiAlH$_4$ (759 mg, 20.00 mmol, 2 eq.) was added as a 1 pellet. After the addition was completed, the reaction mixture was refluxed for 16 h. The reaction mixture was cooled down to 0° C. (ice bath) and carefully quenched with water (50 mL). Formed precipitate was filtered off (2 cm pad of celite on sinter), washed with EtOAc (100 mL) and the combined organic phases were washed with 1 M NaOH (20 mL), dried (K$_2$CO$_3$) and the solvent was removed under reduced pressure to give the corresponding diamine as colourless oil (6.1 g, quant). [Q]$_D^{32}$ −26.4 (c 0.5 in CHCl$_3$); HRMS: found (EI): [M+H]$^+$, 599.3664. C$_{38}$H$_{51}$N$_2$O$_2$S requires: M, 599.3666; δ$_H$(400 MHz, CDCl$_3$) 7.12-7.15 (3H, m, ArH), 6.98 (2H, s, ArH), 6.92-6.96 (1H, m, ArH), 6.85-6.89 (4H, m, ArH), 6.73-6.75 (2H, m, ArH), 6.53 (1H, br. s, NH), 5.70 (2H, s, CH=CH), 5.36 (1H, s, C=CH), 4.41 (1H, d, J=8.0, CHNS), 3.93-4.00 (2H, m, o-CH($^i$Pr)), 3.49 (1H, d, J=8.0, CHNC), 2.83 (1H, sept, J=8.0 and 4.0, p-CH(Pr)), 2.63-2.68 (2H, m, CH$_2$), 2.52-2.56 (2H, m, CH$_2$), 2.43-2.49 (1H, m, CH$_2$), 2.32-2.38 (1H, m, CH$_2$), 1.91-1.97 (2H, m, CH$_2$), 1.49-1.63 (2H, m, CH$_2$), 1.21 (12H, d, J=8.0, o-$^i$Pr(CH$_3$), 1.07 (6H, d, J=4.0, p-$^i$Pr(CH$_3$); δ$_C$ (100 MHz, CDCl$_3$) 152.3, 149.9, 136.6, 138.2, 134.3, 128.2, 127.7, 127.5, 127.5, 127.1, 124.3, 123.2, 118.7, 68.4, 63.0, 46.9, 34.9, 34.2, 29.7, 28.9, 27.6, 26.8, 25.0, 24.7, 23.7, 23.6; m/z (ESI) 599.4 (M$^+$+1, 100%).

Example 14: Di-p-chlorodichlorobis[4-methy-N-[(1S,2S)-2-[methyl[3-(η6-phenyl)propyl]amino]-1,2-diphenylethyl]benzenesulfonamide]diruthenium Hydrochloride, TrisDpen RuCl$_2$ Dimer

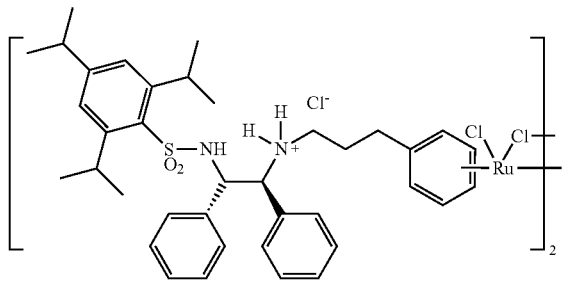

Under argon atmosphere, N-((1S,2S)-2-((3-(cyclohexa-1,4-dien-1-yl)propyl)amino)-1,2-diphenylethyl)-2,4,6-triisopropylbenzenesulfonamide (44.7 g, 65.9 mmol, based on the previous step) was placed in round bottom flask and EtOH (50 mL) was added. To this mixture, solution of RuCl$_3$ (30.4 g of 20% solution in HCl, 59.95 mmol) in EtOH (30 mL) was added at once. Reaction flask was connected to reflux condenser and deoxygenated by 3 vacuum/refill cycles. Resulting mixture was stirred at 75° C. overnight. After cooling, reaction flask was cooled down to −15° C. resulting in formation of red/green precipitate. Mother liquor was decanted and the residue dried in vacuo to give the title compound as red/green solid 52.6 g (quant). mp: 222-224° C. (dec.); δ$_H$ (400 MHz, DMSO-d6) 9.94 (2H, br. s, NH), 9.40 (2H, br. s, NH), 8.88 (2H, d, J=8.5 Hz, NH), 7.36 (4H, br. s, ArH), 7.27 (7H, br. s, ArH), 6.96 (4H, s, TrisCH), 6.79-6.88 (9H, m, ArH), 6.05 (4H, br. s, RuArH), 5.83 (4H, br. s, RuArH), 5.77 (2H, d, J=4.5 Hz, RuArH), 4.90 (2H, t, J=9.0 Hz, C(Ph)HN), 4.70 (2H, br. s, CH(Ph)N+), 3.98-4.01 (4H, m, o-CH(CH$_3$)$_2$), 2.78-2.83 (6H, m, p-CH(CH$_3$)$_2$+ CH$_2$), 2.45-2.63 (4H, m, CH$_2$), 2.11-2.15 (4H, m, CH$_2$), 1.12-1.15 (36H, m, CH(CH$_3$)$_2$); δ$_C$ (100 MHz, DMSO-d6) 151.7, 148.7, 136.1, 134.1, 131.6, 129.2, 129.1, 128.7, 128.3, 128.2, 127.5, 127.3, 126.0, 122.8, 105.8, 88.8, 85.2, 85.1, 83.6, 64.3, 60.2, 44.9, 33.3, 31.9, 29.2, 29.0, 24.9, 24.6, 24.2, 23.4, 23.4; m/z (ESI) 697.2 ([½% M-Cl]$^+$, 100%).

Example 15: Chloro[N-[(1S,2S)-1,2-diphenyl-2-[(S)-[3-(η6-phenyl)propyl]amino-κN]ethyl]-2,4,6-triisopropyl benzene sulfonamidato-κN]-ruthenium (II), [TrisDpen-teth RuCl]

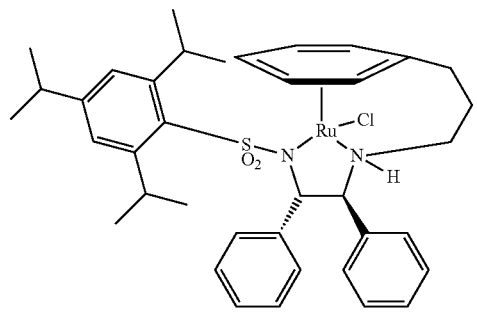

(S,S)-TrisDpen RuCl$_2$ dimer (34.5 g, 22.2 mmol) was placed to 250 mL round bottom flask equipped with nitrogen inlet and atmosphere was exchanged to argon by vacuum-refill cycles. EtOH (60 mL) was added and reaction mixture was deoxygenated by 3 vacuum-refill cycles. i-Pr$_2$EtN (23 mL, 6 eq. 133 mmol) was added which resulted in formation of red precipitate. Reaction mixture was stirred at room temperature for 16 h. Formed red slurry was transferred to Schlenk type sinter and the precipitate was filtered off, washed with EtOH (3×15 mL) and dried to give the title compound as orange powder (16 g, 48%). mp: >231° C. (dec.); [α]$_D^{28}$ −373 (c 0.3 in DMSO); (found (EI): [M-Cl]$^+$, 697.2402. C$_{38}$H$_{47}$N$_2$O$_2$RuS requires: 697.2402); m/z (ESI): 697.2 ([M-Cl]$^+$, 100%). The CDCl$_3$ NMR shows a ratio of 1:1.4 of two isomers; δH (700 MHz, CDCl$_3$) Major: 7.09 (3H, m, ArH), 6.81 (1H, br. s, ArH), 6.70 (3H, d, J=6.2 Hz, ArH), 6.53-6.59 (5H, m, ArH), 6.31-6.33 (1H, m, RuArH), 6.27 (1H, t, J=5.7 Hz, RuArH), 6.20 (1H, t, J=5.9 Hz, RuArH), 5.22 (1H, d, J=5.7 Hz, RuArH), 5.17 (1H, d, J=5.7 Hz, RuArH), 4.95 (1H, t, J=11.4 Hz, NH), 4.41-4.43 (1H, m, CH(CH$_3$)$_2$), 4.27-4.35 (1H, m, CH), 4.15-4.17 (1H, m, CH(CH$_3$)$_2$), 3.54 (1H, t, J=11.4 Hz, CH(Ph)), 2.90-2.94 (2 H, m, CH$_2$), 2.61-2.72 (3H, m, CH(CH$_3$)$_2$+CH$_2$), 1.65 (2H, t, J=6.2 Hz, CH$_2$), 1.13-1.15 (12H, m, o-CH(CH$_3$)$_2$), 1.07 (6H, dd, J=6.8 and 4.2 Hz, CH(CH$_3$)$_2$); Minor: 7.62 (1H, d, J=7.5 Hz, ArH), 7.41 (1H, t, J=7.5 Hz, ArH), 7.20 (1H, t, J=5.3 Hz, ArH), 6.92 (1H, t, J=7.3 Hz, ArH), 6.81-6.83 (3H, br. s, ArH), 6.49-6.51 (4H, m, ArH), 6.38 (1H, t, J=5.3 Hz, RuArH), 6.25 (1H, d, J=7.5 Hz, RuArH), 5.73 (1H, t, J=5.7 Hz, RuArH), 5.46 (1H, d, J=6.2 Hz, RuArH), 5.32 (1H, J=5.3 Hz, RuArH), 4.51-4.52 (2H, m, o-CH(CH$_3$)$_2$), 4.27-4.35 (2H, m, CH(Ph)), 3.01-3.04 (2H, m, CH$_2$), 2.61-2.72 (3H, m, p-CH(CH$_3$)$_2$+CH$_2$), 2.26-2.33 (2H, m, CH$_2$), 1.34 (6H, dd, J=15.4 and 6.2 Hz, CH(CH$_3$)$_2$), 1.22-1.27 (6H, m, CH(CH$_3$)$_2$), 0.99 (6H, d, J=6.6 Hz, CH(CH$_3$)$_2$); δC (176 MHz, CDCl$_3$) Major: 149.7, 149.4, 139.1, 137.8, 137.2, 129.1, 128.7, 128.1, 126.6, 126.4, 126.1, 122.0, 98.5, 92.4, 90.0, 87.0, 81.5, 79.4, 74.5, 69.1, 49.3, 34.0, 29.7, 28.6, 27.9, 23.9, 23.7, 23.6; Minor: 150.3, 147.5, 139.3, 137.9, 137.4, 131.9, 129.1, 128.6, 125.7, 124.5, 122.8, 121.2, 91.5, 88.8, 87.1, 83.7, 79.5, 77.1, 73.0, 70.3, 47.2, 30.3, 29.8, 28.4, 27.7, 27.4, 24.0, 23.7. 19.

Scheme 4: Synthesis of C3-[Tris-EN-teth-RuCl]

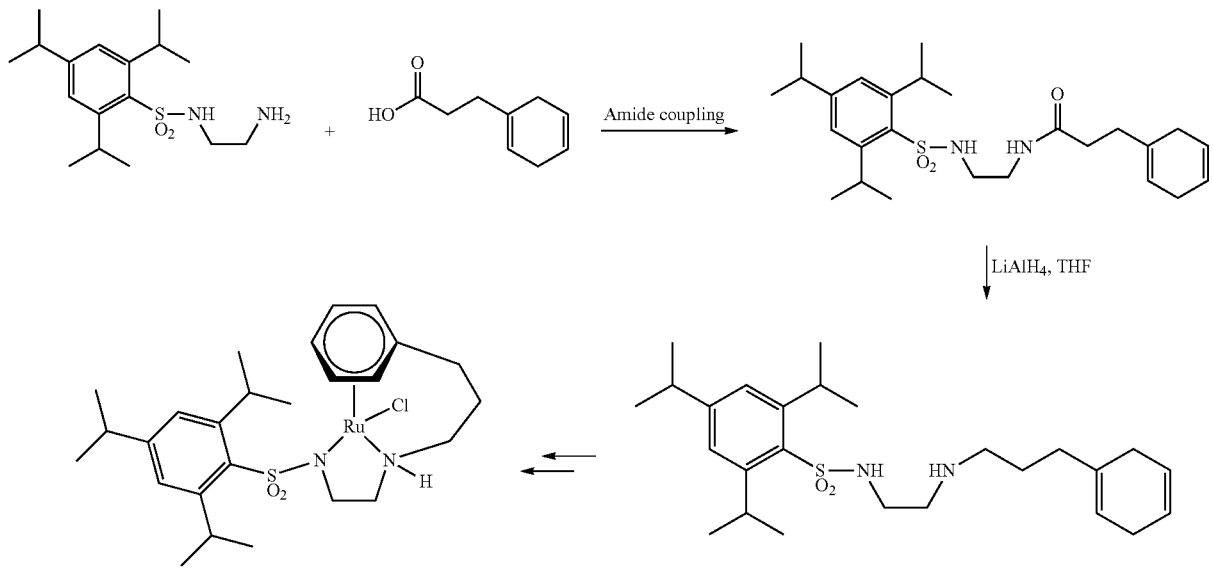

Example 16: 3-(cyclohexa-1,4-dien-1-yl)-N-[2-([2,4,6-tri(propan-2-yl)phenyl]sulfonylamino)ethyl] propanamide

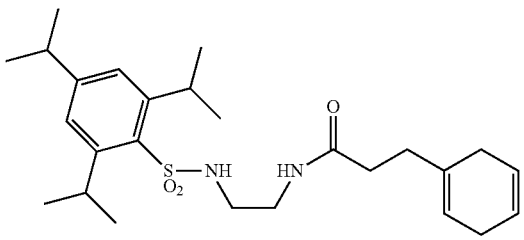 [SMILES: CC(C)c1cc(C(C)C)c(S(=O)(=O)NCCNC(=O)CCC2=CCC=CC2)c(C(C)C)c1]

Example 17: N-[2-(3-Cyclohexa-1,4-dienyl-propylamino)-ethyl]-2,4,6-triisopropyl-benzene Sulphonamide

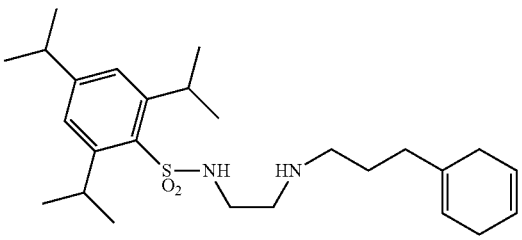 [SMILES: CC(C)c1cc(C(C)C)c(S(=O)(=O)NCCNCCCC2=CCC=CC2)c(C(C)C)c1]

In a round bottom flask were mixed added 3-(cyclohexa-1,4-dien-1-yl)-propionic acid (200 mg, 1.32 mmol), HOBt (195 mg, 1.44 mmol) and TrisEN (457 mg, 1.40 mmol). The reagents were dissolved in anhydrous DMF (4 mL) and anhydrous DCM (4 mL). The solution was cooled to 0° C., then EDC (242 mg, 276 µL, 1.56 mmol) was added. The temperature was maintained for 1 h. The reaction then allowed to warm to rt and left overnight. Water (50 mL) was added and the resulting mixture was extracted using EtOAc (3×50 mL). The combined organic extracts were washed with water (3×100 mL) and brine (3×100 mL), dried with $Na_2SO_3$ and concentrated to give the amide as a white solid (530 mg, 1.16 mmol, 88%). Mp: 118-120° C.; found: [M−H]+, 459.2685. $C_{26}H_{39}N_2O_3S$ requires M, 459.2687; $δ_H$ (400 MHz, $CDCl_3$) 7.17 (2H, s, ArH), 6.77 (1H, t, J=5.5, NH), 5.77 (1H, t, J=6.0, NH), 5.64 (2H, s, CH=CH), 5.39 (1H, br. s, C=CH), 4.06-4.18 (2H, m, o-$^i$Pr(CH)), 3.37-3.44 (2H, m, $CH_2$), 3.06-3.10 (2H, m, $CH_2$), 3.00-3.05 (1H, m, p-$^i$Pr(CH)), 2.85-2.76 (2H, m, $CH_2$), 2.59-2.66 (2H, m, $CH_2$), 2.47-2.55 (2H, m, $CH_2$), 2.22-2.32 (2H, m, $CH_2$), 1.25 (18H, d, J=6.5, $^i$Pr($CH_3$)); $δ_C$ (100 MHz, $CDCl_3$) 174.1, 153.0, 150.3 (2C), 133.5, 131.8, 129.9 (2C), 121.6, 119.1 (2C), 42.5, 38.2, 34.5, 34.2, 33.0, 29.6 (2C), 28.9, 27.0, 24.9 (4C), 23.6 (2C); m/z (ESI): [M−H]+, 459.2 (100%).

To a solution of 2M $LiAlH_4$ in THF (1.3 mL, 2.6 mmol) was added 3-(cyclohexa-1,4-dien-1-yl)-N-[2-([2,4,6-tri(propan-2-yl)phenyl]sulfonylamino)ethyl] propanamide (300 mg, 0.652 mmol), in dry THF (4 mL). The mixture was then heated to reflux (70° C.) and left overnight. The reaction was cooled to room temperature. Water (1 mL) was added with 10% NaOH solution (1 mL). The mixture was the filtered through a plug of celite washing the with plug DCM (50 mL). The aqueous layer was then extracted using DCM (3×50 mL) and dried with $Na_2SO_3$. The DCM was then concentrated to give a white solid (250 mg, 0.561 mmol, 86%). Found (ESI): [M+H]+, 447.3025. $C_{26}H_{43}N_2O_2S$ requires: 447.3040; $δ_H$ (400 MHz, $CDCl_3$) 7.17 (2H, s, ArH), 5.70 (2H, s, CH=CH), 5.41 (1H, br. s, CH=C), 4.14-4.20 (2H, m, o-CH$(Me)_2$), 3.03-3.06 (2H, m, $CH_2NH$), 2.88-2.93 (1H, m, p-CH$(Me)_2$), 2.78-2.80 (2H, m, $CH_2NH_2$), 2.66-2.70 (2H, m, $CH_2$), 2.55-2.59 (4H, m, $CH_2$), 1.97 (2H, t, J=8.0, $CH_2$), 1.57 (2H, quint, J=8.0, $CH_2$), 1.25-1.28 (18H, m, CH$(CH_3)_2$), the NH protons were not observed; $δ_C$ (100 MHz, $CDCl_3$) 152.7 (2C), 152.7 (2C), 150.3, 134.3, 132.2, 124.3, 124.2, 123.8 (2C), 118.8, 49.0, 48.0, 41.9, 35.0, 34.2, 28.9, 29.7 (2C), 27.3, 26.8, 24.9 (4C), 23.6 (2C); m/z (ESI) 447.3 ([M+H]+, 100).

Example 18: Di-p-chlorodichlorobis[N-[2-[[3-($\eta^6$-phenyl)propyl](3-phenylpropyl)amino]ethyl]-4-2,4,6-triisopropylbenzene sulfonamide]diruthenium (II) hydrochloride, Tris-EN RuCl$_2$ Dimer

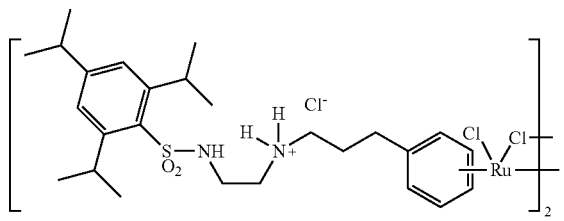

Aqueous acidic RuCl$_3$ solution (140 mg, 0.54 mmol) in ethanol (30 mL) was placed in a round bottom flask. To this a solution of N-[2-(3-cyclohexa-1,4-dienyl-propylamino)-ethyl]-2,4,6-triisopropyl-benzenesulfonamide (300 mg, 0.67 mmol) and 2M HCl in ether (2.7 mL, 5.4 mmol) in DCM (20 mL) was added slowly at room temperature. The solvent was removed to generate the ruthenium dimer (429 mg, 0.32 mmol, 59%) as a brown solid. Mp: 117-119° C. (dec); (found (EI): [% M-Cl]$^+$, 545.1781; requires: C$_{26}$H$_{39}$N$_2$O$_2$RuS, 545.1776); $\delta_H$ (400 MHz, DMSO-d6) 9.14 (2H, br. s), 7.85 (2H, br. s), 7.24 (4H, s, Tris(ArH)), 6.00 (2H, br. s, Ru—ArH), 5.79 (4H, s, Ru—ArH), 4.08 (4H, m, CH-o-($^i$Pr)), 3.12 (4H, br. s, CH$_2$NH$_2$), 2.99 (6H, m, CH$_2$NH$_2$C and p-CH(CH$_3$)$_2$), 2.50 (4H, s, CH$_2$), 1.96 (4H, s, CH$_2$), 1.20 (36H, m, CH$_3$($^i$Pr)); $\delta_C$ (100 MHz, DMSO-d6) 153.2, 149.7 (2C), 132.5, 123.6 (2C), 105.9, 88.7 (2C), 85.2 (2C), 83.6, 46.3, 46.1, 38.0, 33.3, 29.3, 28.8, 24.9 (2C), 24.8 (4C), 23.4 (2C); m/z (ESI): 545.2 ([½% M-Cl]$^+$, 100%).

Example 19: Chloro[N-[2-[(S)-[3-($\eta^6$-phenyl)propyl]amino-κN]ethyl]-2,4,6-triisopropyl benzene sulfonamidato-κN]-ruthenium (II), [TrisEN-teth RuCl]

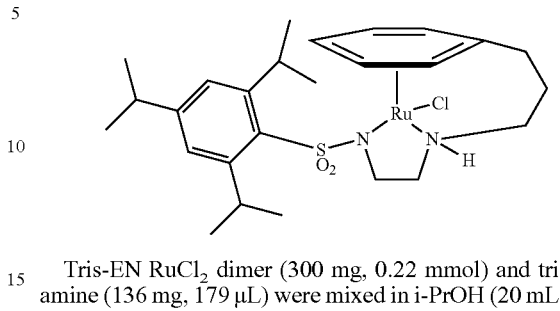

Tris-EN RuCl$_2$ dimer (300 mg, 0.22 mmol) and triethylamine (136 mg, 179 μL) were mixed in i-PrOH (20 mL). The flask was heated to flux and stirred for 90 minutes. The reaction was cooled to room temperature, the solvent was concentrated under reduced pressure, then DCM (50 mL) was added and the solution was washed with water (3×100 mL) and dried over sodium sulphate. DCM was removed under reduced pressure and the desired monomeric complex was isolated as a brown solid. Purification was by column chromatography in DCM to DCM/10% MeOH to yield the target compound (153 mg, 0.26 mmol, 60%). Mp: 113-115° C.; found (EI): [M-Cl]$^+$, 545.1783. requires: C$_{26}$H$_{39}$N$_2$O$_2$RuS, 545.1777; $\delta_H$ (400 MHz, CDCl$_3$) 7.09 (2H, s, TrisCH), 6.67 (1H, t, J=6.0, Ru—ArH), 6.02 (1H, t, J=6.0, Ru—ArH), 5.87 (1H, t, J=6.0, Ru—ArH), 5.17 (1H, d, J=8.0, Ru—ArH), 4.98 (1H, d, J=4.0, Ru—ArH), 4.47-4.53 (2H, m, o-$^i$Pr(CH)), 3.86 (1H, br. s, NH), 3.26-3.32 (1H, m, p-$^i$Pr(CH)), 2.82-2.90 (2H, m, CH$_2$), 2.66-2.74 (2H, m, CH$_2$), 2.46-2.63 (4H, m, CH$_2$), 2.23-2.36 (2H, m, CH$_2$), 1.21-1.28 (18H, m, CH$_3$($^i$Pr)); $\delta_C$ (100 MHz, CDCl$_3$) 150.7, 150.6 (2C), 133.9, 123.2 (2C), 98.1, 92.5, 89.7, 79.4, 77.0, 73.9, 57.3, 52.2, 47.2, 34.0, 29.5, 29.0, 25.4 (2C), 25.0 (4C), 23.7 (2C); m/z (ESI): 545.2 ([M-Cl]$^+$, 100%).

Scheme 5: Alternative Synthesis of [Tris-EN-teth-RuCl]

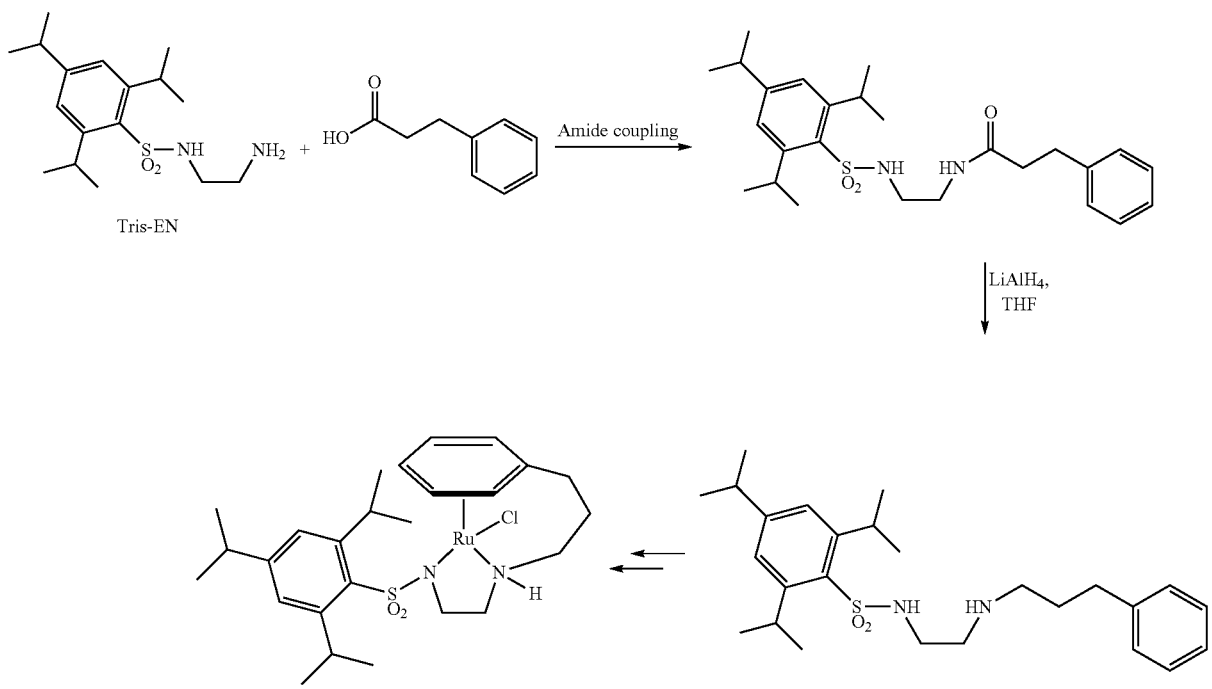

Example 20: 3-Phenyl-N-[2-(2,4,6-triisopropyl-benzenesulfonylamino)-ethyl]-propionamide

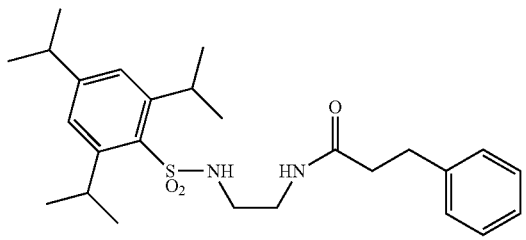 [SMILES: CC(C)c1cc(C(C)C)c(S(=O)(=O)NCCNC(=O)CCc2ccccc2)c(C(C)C)c1]

Prepared using the general procedure of example 8 from 3-phenylpropanoic acid (1.00 g, 6.66 mmol) with TrisEN (2.38 g, 7.30 mmol), HOBt (0.99 g, 7.33 mmol) and EDC (1.23 g, 7.93 mmol). The product was obtained as a white solid (2.15 g, 4.69 mmol, 71%); found (EI): [M+Na]+, 481.2492; $C_{26}H_{38}N_2NaO_3S$ requires: 481.2495; 6H (400 MHz, CDCl$_3$) 7.21-7.26 (2H, m ArH), 7.13-7.16 (5H, m, ArH), 6.37 (1H, t, J=5.8, NH—CO), 5.31 (1H, t, J=6.3, NH—S), 4.11 (2H, spt, J=6.0, o-iPr(CH)) 3.35-3.39 (2H, m, CH$_2$N), 3.00-3.3.04 (2H, m, CH$_2$NCO), 2.68-2.94 (3H, m, CH$_2$ and p-iPr(CH)), 2.47 (2H, t, J=15.6, CH$_2$), 1.25 (18H, d, J=6.5, iPr(CH$_3$)); $\delta_C$ (100 MHz, CDCl$_3$) 173.2, 153.0, 150.3 (2C), 140.8, 131.8, 128.5 (2C), 128.4 (2C), 126.2, 123.9 (2C), 42.6, 39.5, 38.2, 34.2, 31.7, 29.6 (4C), 24.9 (2C), 23.6 (2C); m/z (ESI): 481.2 ([M+Na]+, 100%).

Example 21: 2,4,6-Triisopropyl-N-[2-(3-phenyl-propylamino)-ethyl]-benzenesulfonamide

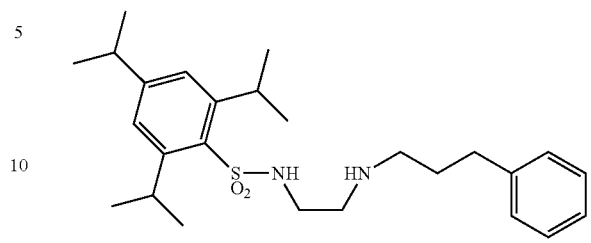

Prepared using the procedure of example 9 with 3-phenyl-N-[2-(2,4,6-triisopropyl-benzenesulfonylamino)-ethyl]-propionamide (1.00 g, 2.18 mmol) and 2 M LiAlH$_4$ in THF (4.4 mL, 8.8 mmol) in anhydrous THF (20 mL) to yield an off-white solid (1.04 g, quant.). Mp: 70-72 OC; found (EI): [M+Na]+, 467.2709. $C_{26}H_{40}N_2NaO_2S$ requires: M, 467.2703; $\delta_H$(400 MHz, CDCl$_3$) 7.25-7.29 (2H, m, ArH), 7.14-7.19 (3H, m, ArH), 7.16 (2H, s, TrisArH), 4.18 (2H, spt, J=6.8, o-iPr(CH)), 2.99-3.02 (2H, m, CH$_2$N), 2.89 (1H, spt, J=6.9, p-iPr(CH)), 2.72 (2H, dd, J=6.3 and 4.8, CH$_2$), 2.61 (2H, t, J=15.6, CH$_2$), 2.55 (2H, t, J=7.0, CH$_2$), 1.70-1.78 (2H, m, CH$_2$), 1.24-1.27 (18H, m, iPr(CH$_3$); $\delta_C$ (100 MHz, CDCl$_3$) 152.6, 150.3 (2C), 141.9, 132.3, 128.4 (2C), 128.3 (2C), 125.9, 123.8 (2C), 48.9, 48.0, 42.2, 34.1, 33.6, 31.7, 29.7 (4C), 24.9 (2C), 23.6 (2C); m/z (ESI): 445.2 ([M+H]+, 100%).

The subsequent synthetic steps to prepare [Tris-EN-teth RuCl] may be carried out as described in the literature: R. Soni, K. E. Jolley, M. Wills, *Organic Lett*. 2013, 15, 5110-5113.

Scheme 6: Synthesis of C4- [Tris-Dpen-teth-RuCl]

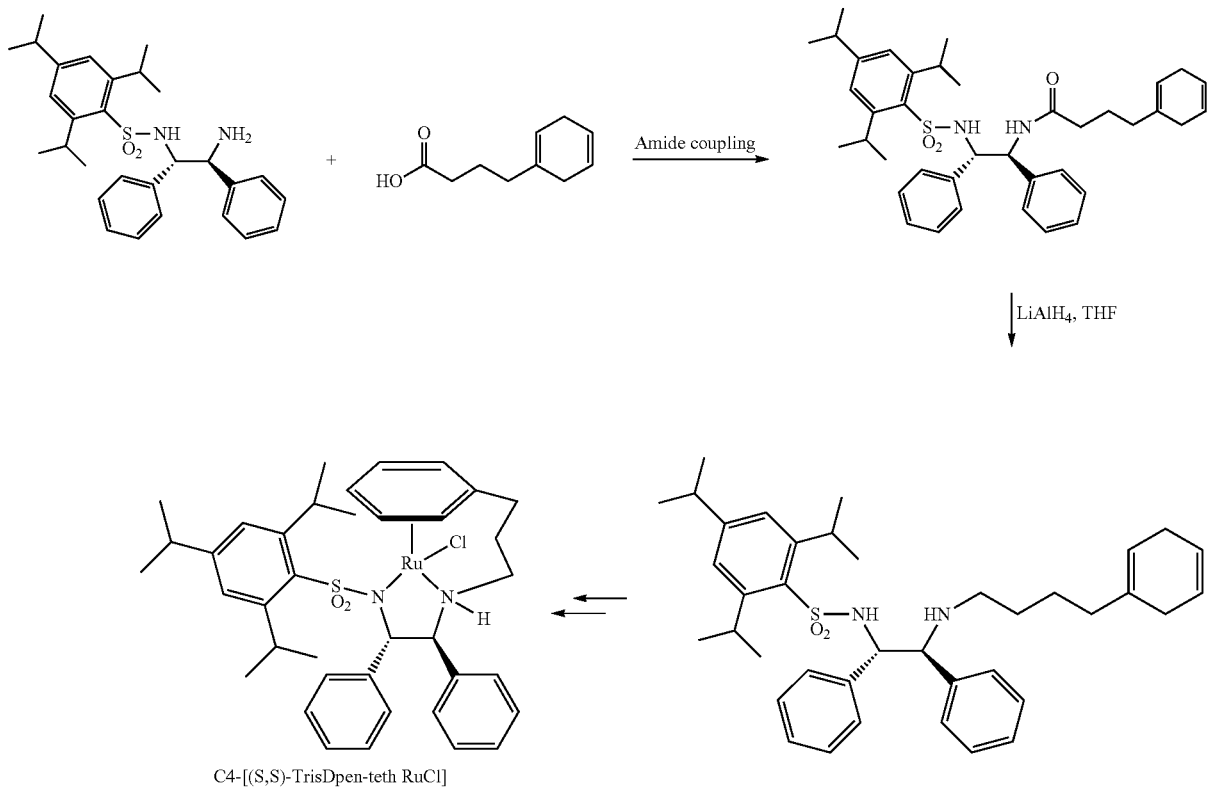

C4-[(S,S)-TrisDpen-teth RuCl]

Example 22: 4-(cyclohexa-1,4-dien-1-yl)-N-((1S,2S)-1,2-diphenyl-2-(2,4,6-triisopropylphenyl sulfonamido) ethyl)butanamide

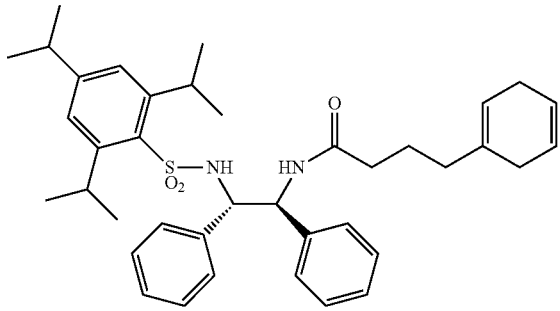 [SMILES: CC(C)c1cc(C(C)C)c(S(=O)(=O)N[C@@H](c2ccccc2)[C@@H](NC(=O)CCCC2=CCC=CC2)c2ccccc2)c(C(C)C)c1]

4-Cyclohexa-1,4-dienyl-butanoic acid (1.66 g, 10.00 mmol) was dissolved in dry Me-THF (30 mL) and N-methylmorpholine (1.01 mL, 10.00 mmol) was added. The reaction mixture was cooled down to −15° C. and a solution of i-butyl chloroformate (1.36 g, 1.30 mL, 10.00 mmol) in THF (5 mL) was added dropwise over a period of 15 min. After addition was completed, the mixture was stirred at −15° C. for another 15 min and the (S,S)-Tris-DPEN (4.78, 10.00 mmol, 1 eq.) in Me-THF (20 mL) was added at once. The cooling was then removed and the reaction mixture was allowed to warm up to r.t. and stirred overnight. The solvent was removed under reduced pressure and the remaining rest was diluted with EtOAc (40 mL), washed with 10% $Na_2CO_3$ (50 mL), 0.1 M HCl (50 mL), brine (50 mL) and dried over magnesium sulphate. The solvent was removed under reduced pressure to give the amide as white solid (6.46 g, quant.). δH (400 MHz, $CDCl_3$) 7.10-7.05 (3H, m, ArH), 6.95-6.90 (5H, m, ArH), 6.90-6.82 (2H, m, ArH), 6.77-6.70 (1H, m, ArH), 6.62-6.56 (2H, m, ArH), 5.84 (1H, d, J=8.1 Hz), 5.67-5.58 (2H, m, CH=CH), 5.38-5.34 (1H, m, C=CH), 5.17 (1H, dd, J, =11, $J_2$=7.6 Hz, CHPh), 4.40 (1H, dd, J, =11, $J_2$=7.6 Hz, CHPh), 3.97-3.84 (2H, m, $CH(CH_3)_2$), 2.68-2.68 (1H, m, $CH(CH_3)_2$), 2.64-2.48 (4H, m, $CH_2$), 2.34-2.17 (2H, m, $CH_2$); 2.00-1.92 (2H, m, $CH_2$), 1.83-1.72 (2H, m, $CH_2$), 1.1 (12H, dd, J, =6.3 Hz, $J_2$=7.2 Hz, CH$(CH_3)_2$)) 0.9 (6H, J=6.7 Hz, $CH(CH_3)_2$); $δ_C$ (100 MHz, $CDCl_3$) 174.4 (NHCO), 152.7, 149.9, 138.9, 138.2, 134.1, 133.2, 128.5, 128.2, 127.7, 127.4, 127.3, 124.4, 124.2, 123.5, 119.2, 62.9, 58.4, 36.8, 36.1, 34.1, 29.7, 28.7, 26.7, 25.0, 24.3, 23.6, 23.6, 23.0.

Example 23: N-((1S,2S)-2-((4-(cyclohexa-1,4-dien-1-yl)butyl)amino)-1,2-diphenylethyl)-2,4,6-triisopropylbenzenesulfonamide

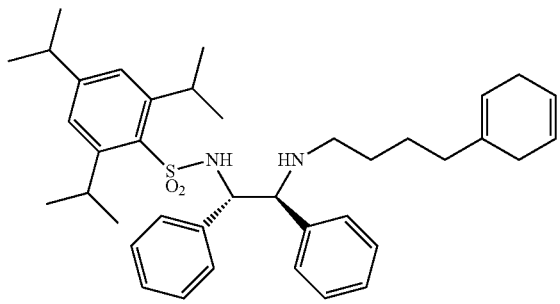 [SMILES: CC(C)c1cc(C(C)C)c(S(=O)(=O)N[C@@H](c2ccccc2)[C@@H](NCCCCC2=CCC=CC2)c2ccccc2)c(C(C)C)c1]

4-(Cyclohexa-1,4-dien-1-yl)-N-((1S,2S)-1,2-diphenyl-2-(2,4,6-triisopropylphenylsulfonamido) ethyl)butanamide (6.26 g, 10.00 mmol) was dissolved in dry Me-THF (100 mL) and $LiAlH_4$ (759 mg, 20.00 mmol, 2 eq.) was added as a 1 pellet. After the addition was completed, the reaction mixture was refluxed for 16 h. The reaction mixture was cooled down to 0° C. (ice bath) and carefully quenched with water (50 mL). Formed precipitate was filtered off (2 cm pad of celite on sinter), washed with EtOAc (100 mL) and the combined organic phases were washed with 1 M NaOH (20 mL), dried ($K_2CO_3$) and the solvent was removed under reduced pressure to give the corresponding diamine as colourless oil (5.2 g, 85%). $[α]_D^{30}$ −29.3 (c 0.59 in $CHCl_3$); found (ES): ($M^+$+1) 613.3815. $C_{39}H_{53}N_2O_2S$ requires: ($M^+$) 613.3822; $δ_H$ (400 MHz, $CDCl_3$) 7.12-7.14 (3H, m, ArH), 6.98 (2H, s, TrisArH), 6.92-6.96 (1H, m, ArH), 6.84-6.88 (4H, m, ArH), 6.73-6.75 (2H, m, ArH), 5.69 (2H, s, CH=CH), 5.37 (1H, br. s, C=CH), 4.41 (1H, d, J=9.0, CH(Ph)NS), 3.92-3.99 (2H, m, o-$CH(CH_3)_2$), 3.50-3.59 (1H, m, CH(Ph)NH), 2.83 (1H, dt, J=13.7 and 7.0, p-CH$(CH_3)_2$), 2.64-2.69 (2H, m, $CH_2$), 2.50-2.58 (2H, m, $CH_2$), 2.43-2.48 (1H, m, $CH_2$), 2.32-2.40 (1H, m, $CH_2$), 1.89-1.92 (2H, m, $CH_2$), 1.36 (2H, m, $CH_2$), 1.21 (12H, dd, J=6.8 and 2.3, o-, p-$^iPr$(Me)), 1.07 (6H, d, J=6.5, o-$^iPr$(Me)); $δ_C$ (100 MHz, $CDCl_3$) 152.4, 149.9, 139.4, 138.2, 133.9, 129.4, 128.5, 128.3 (2), 127.7, 127.6, 127.6 (2), 127.5, 127.1, 125.4, 124.3, 123.2, 118.6, 68.2, 62.9, 47.1, 37.2, 34.2, 28.9, 26.8, 25.0, 24.8, 24.7, 23.7, 23.6; m/z (ESI): 613.3 ($M^+$+1, 100%).

Example 24: N—[(S,S)-1,2-Diphenyl-2-(4-phenyl-butylamino)-ethyl]-(2,4,6-triisopropylphenyl)-sulfonamide Ammonium Chloride Ruthenium Dimer

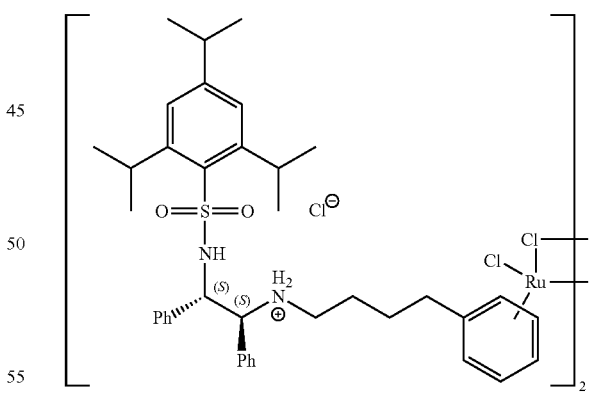

Under an argon atmosphere, N-((1S,2S)-2-((4-(cyclohexa-1,4-dien-1-yl)butyl)amino)-1,2-diphenylethyl)-2,4,6-triisopropylbenzenesulfonamide (116.58 g, 163 mmol, 86% pure based on $^1$H-NMR) was placed in 500 mL round bottom flask and EtOH (150 mL) was added. To this mixture, solution of $RuCl_3$ (78.55 g, 155.26 mmol Ru) in EtOH (90 mL) was added at once. Reaction flask was connected to reflux condenser, deoxygenated by 3 vacuum/refill cycles and the resulting mixture was stirred at 75° C. overnight.

Caution:

After ca. 2 h sudden exothermic reaction has occurred. This warmed up the bath to 80° C. Exothermic reaction can be partially controlled by performing the reaction in larger flask.

The rude dark green mixture was filtered over combined pad of $SiO_2$ (1 cm) and celite (2 cm) after filtration, green precipitate formed immediately. This was isolated by decantation and dried to give first crop as green solid (6.77 g, 5.3%). Mother liquor was cooled down to −15° C. overnight to give substantial amount of green/red solid. This was isolated by decantation followed by drying to give the second crop as red/green solid (85 g, 67% theory). Remaining red mother liquor was cooled down to −15° C. again for several days. Red solid precipitated which was separated by decantation followed by drying to give the third crop as red solid 49 g. mp: 222-224° C. (dec.); δH (500 MHz, DMSO-d6) 9.57 (2H, br. s, NH), 9.08 (2H, br. s, NH), 8.65 (2H, d, J=9.1 Hz, NH), 7.28 (4H, br. s, ArH), 7.23 (7H, br. s, ArH), 6.93 (4H, s, TrisArH), 6.79-6.84 (6H, m, ArH), 6.71 (3H, br. s, ArH), 6.00 (4H, br. s, RuArH), 5.75 (6H, br. s, RuArH), 4.74 (2H, br. s, $CH(CH_3)_2$), 4.59 (2H, br. s, $CH(CH_3)_2$), 3.94 (4H, br. s, $CH_2N^+$), 3.68 (2H, br. s, $CH(CH_3)_2$), 2.44 (4H, br. s, $CH_2$), 1.82 (4H, br. s, $CH_2$), 1.73 (4H, br. s, $CH_2$), 1.13 (12H, d, J=6.0 Hz, $CH(CH_3)_2$), 1.09 (12H, d, J=6.3 Hz, $CH(CH_3)_2$), 1.04 (12H, d, J=6.0 Hz, $CH(CH_3)_2$); δC (125 MHz, DMSO-d6) 151.9, 148.8, 135.9, 135.8, 131.7, 129.3, 129.1, 128.8, 128.4, 127.6, 127.3, 125.5, 122.9, 107.3, 89.1, 85.1, 83.4, 64.3, 60.1, 45.6, 33.3, 31.8, 25.8, 24.8, 24.7, 24.5, 23.4; m/z (ESI): 711.1 (% $M^+$-Cl, 100%).

Example 25: N—[(S,S)-1,2-Diphenyl-2-(4-phenylbutylamino)-ethyl]-4-(2,4,6-triisopropyl Benzenesulfonamide Ammonium Chloride Ruthenium Monomer

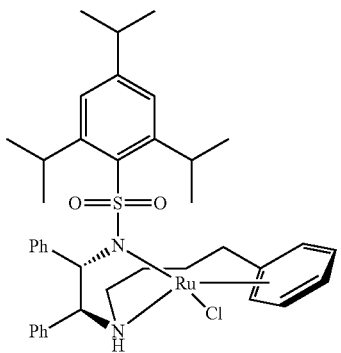

A 500 mL round bottom flask containing N—[(S,S)-1,2-Diphenyl-2-(4-phenylbutylamino)-ethyl]-(2,4,6-triisopropylphenyl)-sulfonamide ammonium chloride ruthenium dimer (86 g, 52.67 mmol) was equipped with magnetic stirrer and EtOH (150 mL) was added. The Ru dimer suspended into the ethanol with help of spatula. The reaction mixture was deoxygenated by 3 additional vacuum-refill cycles. $IPr_2EtN$ (6 eq. 316.02 mmol, 40.85 g, 55.05 mL) was added. Reaction mixture turned to homogeneous dark solution and after ca minutes red precipitate has formed. Stirring was continued for three h. Formed slurry was transferred to Schlenk type sinter and the precipitate was filtered off. Dark mother liquor obtained by filtration was analysed to confirm it does not contain any product. Red precipitate was washed with EtOH (100 mL) until the filtrate was red and dried to give the title compound as pale red powder 35 g (44.5%) mp: >165° C.; (found: $M^+$-Cl, 711.2564. requires $C_{39}H_{49}N_2O_2RuS$: 711.2563); $[α]_D^{32}$ +650 (c=0.0025 in $CHCl_3$); $ν_{max}$ 3062.0, 3027.8, 2927.3, 2867.0, 1600.0, 1559.4, 1494.0, 1453.5, 1379.7, 1315.4, 1265.8, 1150.3, 1108.4, 1076.0, 1039.7 m/z (ESI): 711.1 ($M^+$-Cl, 100%).

The NMR in $CDCl_3$ contains a mixture of 2:1 isomers. The NMR is complex with very flat peaks that are hiding proton signals so not all protons are accounted for. $δ_H$ (700 MHz, $CDCl_3$) Major: 7.12 (1H, t, J=7.3, ArH), 7.01 (2H, br. s, ArH), 6.75 (1H, br. s, ArH), 6.68 (1H, br. s, ArH), 6.52-6.55 (3H, m, ArH), 6.46-6.48 (2H, m, ArH), 6.32 (1H, br. s, RuArH), 6.24 (1H, br. s, RuArH), 6.01 (1H, br. s, RuArH), 5.44 (1H, d, J=5.3 Hz, RuArH), 5.35 (1H, d, J=5.3 Hz, RuArH), 4.52 (1H, br. s, NH), 4.38 (1H, br. s, o-iPr(CH)), 4.20-4.23 (1H, m, CH(Ph)), 3.99 (1H, br. s, o-iPr(CH)), 3.62 (1H, t, J=11.7 Hz, CH(Ph)), 3.40 (1H, t, J=10.0 Hz, $CH_2$), 3.19-3.20 (1H, m, $CH_2$), 2.56-2.74 (3H, m, p-iPr(CH) and $CH_2$), 2.31-2.35 (1H, m, $CH_2$), 2.12-2.14 (1H, m, $CH_2$), 1.92-1.93 (1H, m, $CH_2$), 1.71 (1H, br. s, $CH_2$), 1.40-1.41 (3H, m, $CH_3$), 1.29-1.30 (3H, m, $CH_3$), 1.24-1.27 (3H, m, $CH_3$), 1.13 (6H, t, J=6.4, $CH_3$), 1.10 (6H, m, $CH_3$), 1.07 (3H, t, J=5.9 Hz, $CH_3$); Minor: 7.52 (1H, br. s, ArH), 7.34 (1H, br. s, ArH), 7.03-7.04 (2H, m, ArH), 6.88 (1H, br. s, RuArH), 6.83 (2H, m, ArH), 6.57-6.58 (2H, m, ArH), 6.40 (2H, br. s, ArH), 6.09 (2H, t, J=5.3 Hz, RuArH), 5.51 (2H, d, J=5.3 Hz, RuArH), 5.19 (1H, d, J=5.3 Hz, RuArH), 4.99 (1H, br. s, NH), 4.38 (1H, br. s, o-iPr(CH), 4.20-4.23 (1H, m, CH(Ph)), 4.09 (1H, t, J=11.2 Hz, CH(Ph)), 3.99 (1H, br. s, o-iPr(CH)), 3.68-3.74 (1H, m, $CH_2$), 2.87-2.91 (2H, m, $CH_2$), 2.66-2.74 (1H, m, $CH_2$), 2.56-2.69 (1H, m, p-iPr (CH)), 1.77 (2H, s, $CH_2$), 1.18-1.27 (9H, br. m, $CH_3$), 0.91 (6H, br. s, $CH_3$). $δ_C$ (176 MHz, $CDCl_3$) Major: 149.3, 137.9 (2C), 137.6 (2C), 137.1 (2C), 129.0 (2C), 127.9 (2C), 126.4 (2C), 126.0 (2C), 122.0 (2C), 100.1, 93.6, 84.4, 79.2, 72.0, 69.6, 50.4, 34.0 (2C), 29.6, 28.4, 26.1, 24.2, 23.9 (4C), 23.7 (2C); Minor: 149.4, 147.5, 139.6 (2C), 138.9, 136.1, 128.9 (2C), 128.4, 128.1, 126.5 (2C), 125.9 (2C), 122.9 (2C), 121.0 (2C), 101.4, 89.9, 88.2, 78.9, 77.9, 76.8, 75.6, 72.8, 54.1, 32.1, 30.0, 29.8, 28.6, 27.6, 27.2, 23.7, 23.6 (2C), 22.4, 20.5.

The NMR in DMSO-d6 shows one major isomer and there is evidence for a minor isomer. $δ_H$(700 MHz, DMSO-d6) 8.05 (1H, br. s, ArH), 7.38 (1H, br. s, ArH), 7.06 (1H, t, J=7.3 Hz, ArH), 6.83 (1H, s, ArH), 6.73-6.75 (2H, m, ArH), 6.45 (2H, d, J=6.2 Hz, ArH), 6.32-6.39 (4H, m, ArH), 5.91-5.92 (1H, m, RuArH), 5.88-5.89 (1H, m, RuArH), 5.77 (2H, d, J=5.7 Hz, RuArH), 5.30 (1H, d, J=4.8 Hz, RuArH), 4.52-4.54 (1H, m, o-iPr(CH)), 4.15 (1H, d, J=11.0 Hz, CH(Ph)), 3.87-3.95 (3H, m, CH(Ph) and oiPr(CH)), 2.99 (1H, dd, J=15.4 Hz and 9.7 Hz, $CH_2$), 2.66 (1H, dd, J=15.4 and 10.6 Hz, $CH_2$), 2.57-2.62 (2H, m, p-iPr(CH) and $CH_2$), 2.41-2.46 (1H, m, $CH_2$), 1.90-1.91 (1H, m, $CH_2$), 1.59 (1H, br. s, $CH_2$), 1.49 (1H, br. s, $CH_2$), 1.37 (3H, d, J=5.7 Hz, $iPr(CH_3)$), 1.22 (3H, d, J=5.7 Hz, $iPr(CH_3)$), 1.04-1.05 (6H, m, $iPr(CH_3)$), 0.93 (3H, d, J=5.7 Hz, $iPr(CH_3)$), 0.8 (3H, d, J=5.7 Hz, $iPr(CH_3)$); $δ_C$ (176 MHz, DMSO-d6) 149.8, 148.6, 146.8, 140.3, 140.1, 138.5, 126.1 (2C), 127.9, 126.3 (2C), 125.7, 122.6, 120.6, 103.2, 92.0, 86.7, 79.7, 77.7, 76.2, 74.3, 71.3, 54.3, 33.8, 31.0, 29.5, 29.1, 28.1 (2C), 27.7, 25.0, 24.2 (2C), 23.9, 22.7, 20.2.

Scheme 7: alternative synthesis of C3- [Tris-EN-teth-RuCl]

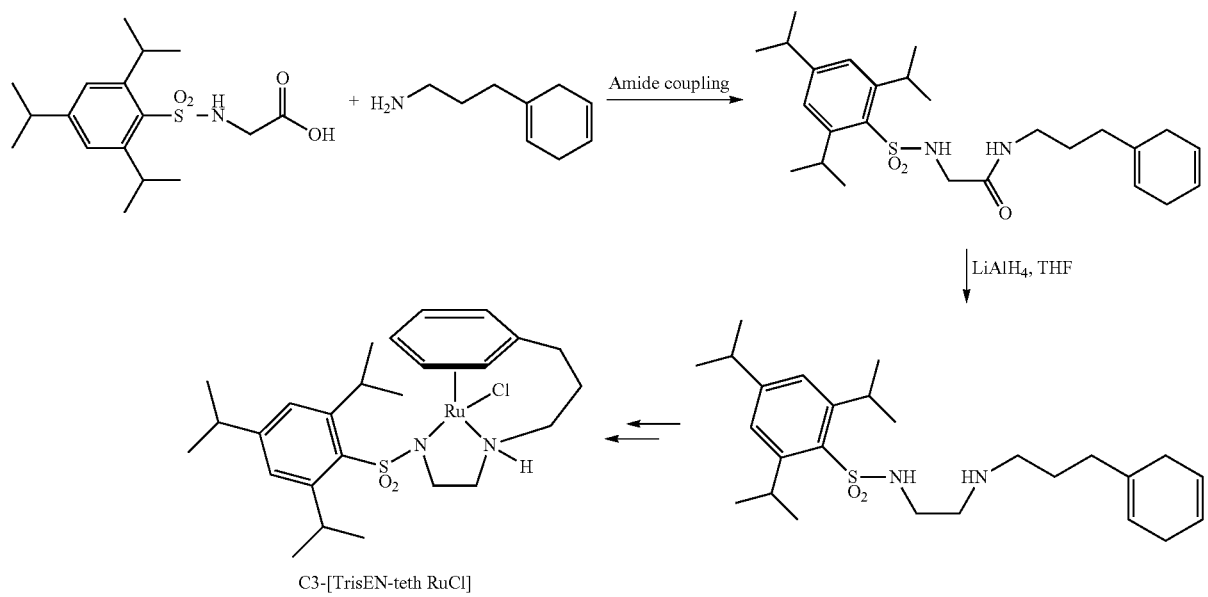

Example 26: N-(3-Cyclohexa-1,4-dienyl-propyl)-2-(2,4,6-triisopropyl-benzenesulfonyl)-glycinamide

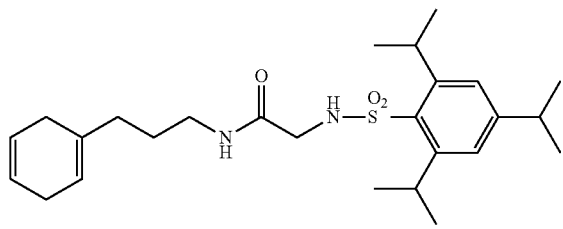 [SMILES: CC(C)c1cc(C(C)C)c(S(=O)(=O)NCC(=O)NCCCC2=CCC=CC2)c(C(C)C)c1]

N-[2,4,6-tri(propan-2-yl)phenyl]sulfonyl-glycine (3.41 g, 10.00 mmol) was dissolved in dry Me-THF (30 mL) and N-methylmorpholine (1.01 mL, 10.00 mmol) was added. The reaction mixture was cooled down to −15° C. and a solution of i-butyl chloroformate (1.36 g, 1.30 mL, 10.00 mmol) in THF (5 mL) was added dropwise over a period of 15 min. After addition was completed, the mixture was stirred at −15° C. for another 15 min and the 3-(cyclohexa-1,4-dien-1-yl)propan-1-amine (1.37 g, 10.00 mmol, 1 eq.) was added at once. The cooling was then removed and the reaction mixture was allowed to warm up to r.t. and stirred overnight. The solvent was removed under reduced pressure and the residue was diluted with EtOAc (40 mL), washed with 10% $Na_2CO_3$ (50 mL), 0.1 M HCl (50 mL), brine (50 mL) and dried over magnesium sulphate. The solvent was removed under reduced pressure to give the amide as white gummy solid (5 g, 108%).

Example 27: N-[2-(3-Cyclohexa-1,4-dienyl-propylamino)-ethyl]-2,4,6-triisopropyl-benzenesulfonamide

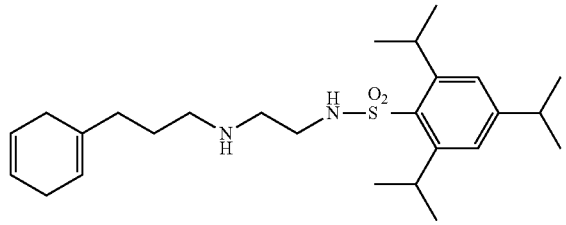 [SMILES: CC(C)c1cc(C(C)C)c(S(=O)(=O)NCCNCCCC2=CCC=CC2)c(C(C)C)c1]

N-(3-Cyclohexa-1,4-dienyl-propyl)-2-(2,4,6-triisopropyl-benzenesulfonyl)-glycinamide (4.6 g, 10.00 mmol) was dissolved in dry Me-THF (100 mL) and $LiAlH_4$ (759 mg, 20.00 mmol, 2 eq.) was added as a 1 pellet. After the addition was completed, the reaction mixture was heated to 80° C. for 16 h. The reaction mixture was cooled down to 0° C. (ice bath) and carefully quenched with water (50 mL). The resulting precipitate was filtered off (2 cm pad of celite on sinter), washed with EtOAc (100 mL) and the combined organic phases were washed with 1 M NaOH (20 mL), dried ($K_2CO_3$) and the solvent was removed under reduced pressure to give the corresponding diamine as colourless oil. Found (ESI): $[M+H]^+$, 447.3025. $C_{26}H_{43}N_2O_2S$ requires: 447.3040; $\delta_H$ (400 MHz, $CDCl_3$) 7.17 (2H, s, ArH), 5.70 (2H, s, CH=CH), 5.41 (1H, br. s, CH=C), 4.14-4.20 (2H, m, o-CH(Me)$_2$), 3.03-3.06 (2H, m, $CH_2NH$), 2.88-2.93 (1H, m, p-CH(Me)$_2$), 2.78-2.80 (2H, m, $CH_2NH_2$), 2.66-2.70 (2H, m, $CH_2$), 2.55-2.59 (4H, m, $CH_2$), 1.97 (2H, t, J=8.0, $CH_2$), 1.57 (2H, quint, J=8.0, $CH_2$), 1.25-1.28 (18H, m, $CH(CH_3)_2$), the NH protons were not observed; $\delta_C$ (100 MHz, $CDCl_3$) 152.7 (2C), 152.7 (2C), 150.3, 134.3, 132.2, 124.3, 124.2, 123.8 (2C), 118.8, 49.0, 48.0, 41.9, 35.0, 34.2, 28.9, 29.7 (2C), 27.3, 26.8, 24.9 (4C), 23.6 (2C); m/z (ESI) 447.3 $([M+H]^+, 100)$.

The subsequent synthetic steps to prepare C3-[Tris-EN teth Ru Cl] may be carried out as described in Example 18 and 19.

Scheme 8: alternative synthesis of C4- [Tris-EN-teth-RuCl]

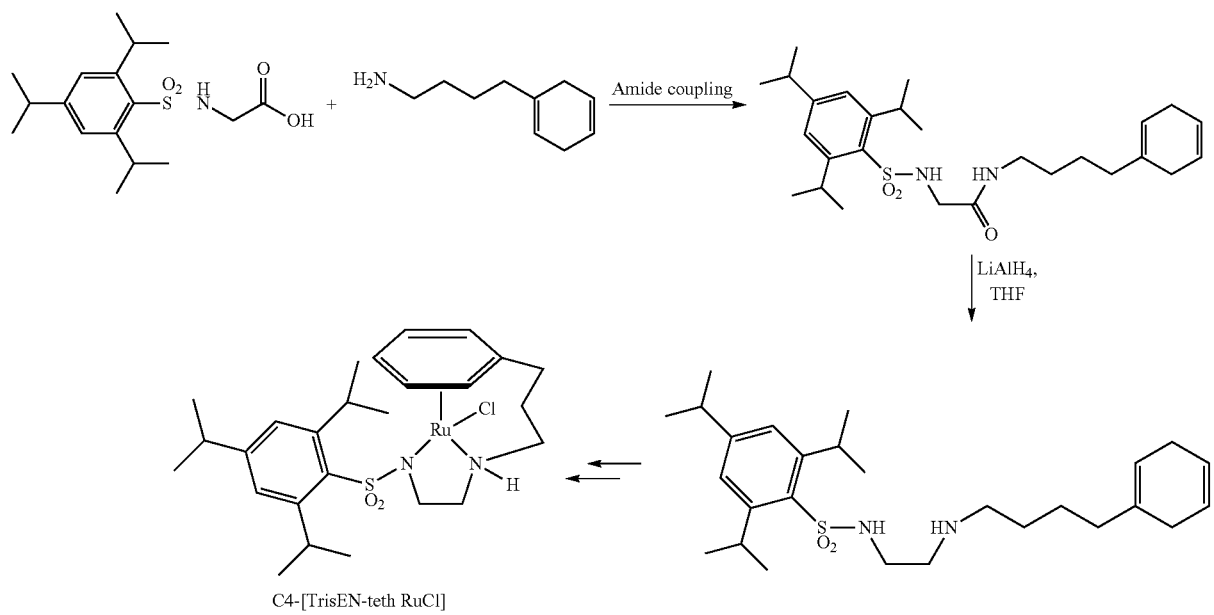

Example 28: N-(3-Cyclohexa-1,4-dienyl-butyl)-2-(2,4,6-triisopropyl-benzenesulfonyl)-glycinamide Example 29: N-[2-(3-Cyclohexa-1,4-dienyl-butylamino)-ethyl]-2,4,6-triisopropyl-benzenesulfonamide

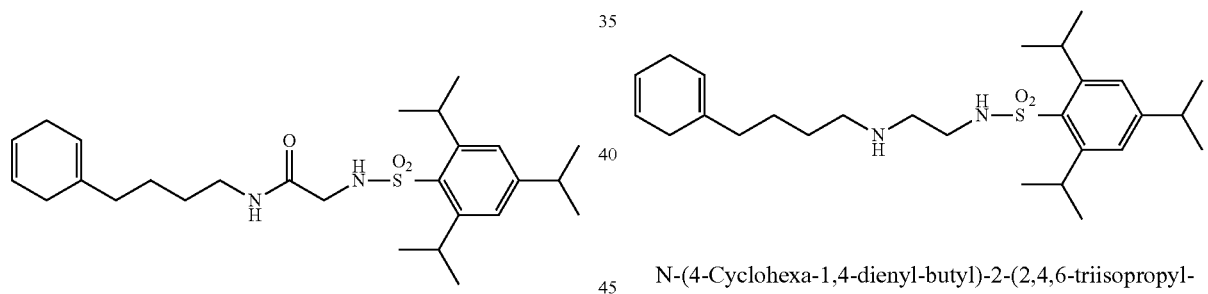

N-[2,4,6-tri(propan-2-yl)phenyl]sulfonyl-glycine (3.41 g, 10.00 mmol) was dissolved in dry Me-THF (30 mL) and N-methylmorpholine (1.01 mL, 10.00 mmol) was added. The reaction mixture was cooled down to −15° C. and a solution of i-butyl chloroformate (1.36 g, 1.30 mL, 10.00 mmol) in THF (5 mL) was added dropwise over a period of 15 min. After addition was completed, the mixture was stirred at −15° C. for another 15 min and the 3-(cyclohexa-1,4-dien-1-yl)propan-1-amine (1.37 g, 10.00 mmol, 1 eq.) was added at once. The cooling was then removed and the reaction mixture was allowed to warm up to r.t. and stirred overnight. The solvent was removed under reduced pressure and the residue was diluted with EtOAc (40 mL), washed with 10% $Na_2CO_3$ (50 mL), 0.1 M HCl (50 mL), brine (50 mL) and dried over magnesium sulphate. The solvent was removed under reduced pressure to give the amide as white gummy solid (5.15 g, 108%).

N-(4-Cyclohexa-1,4-dienyl-butyl)-2-(2,4,6-triisopropyl-benzenesulfonyl)-glycinamide (5.10 g, 10.00 mmol) was dissolved in dry Me-THF (100 mL) and $LiAlH_4$ (759 mg, 20.00 mmol, 2 eq.) was added as a 1 pellet. After the addition was completed, the reaction mixture was heated to 80° C. for 16 h. The reaction mixture was cooled down to 0° C. (ice bath) and carefully quenched with water (50 mL). Formed precipitate was filtered off (2 cm pad of celite on sinter), washed with EtOAc (100 mL) and the combined organic phases were washed with 1 M NaOH (20 mL), dried ($K_2CO_3$) and the solvent was removed under reduced pressure to give the corresponding diamine as colourless oil.

The subsequent synthetic steps to prepare C4-[Tris-EN-teth RuCl] may be carried out as described in Example 18 and 19.

REFERENCES

A number of publications are cited above in order to more fully describe and disclose the invention and the state of the art to which the invention pertains. Full citations for these references are provided below. The entirety of each of these references is incorporated herein.

*ChemFiles* 2007, 4, No. 2, Sigma-Aldrich
*Eur. J. Inorg. Chem.* 2003, 1873-1882
Fujimoto et al. *J. Med. Chem.* 1989 32 1259
Hayes et al. *J. Am. Chem. Soc.,* 2005, 127, 7318-7319
Jolley et al. *Adv. Synth. Catal.,* 2012, 354, 2545-2555
Jolley et al. *Adv. Synth. Catal.,* 2012, 354, 2545-2555
Martins et al. *Tetrahedron Lett.* 2009, 50, 688-692
Snider and Kirk *J. Am. Chem. Soc.* 1983, 105, 2364-2368
Soni et al. *Organic Lett.* 2013, 15, 5110-5113
Tan et al. *Tetrahedron* 2011, 67, 6206-6213
WO 2010/106364
WO 2012/026201
WO 2014/068331

The invention claimed is:

1. A method of preparing an amine compound of formula (I), the method comprising the steps of reducing an amide of formula (II) with a reducing agent to form the amine compound of formula (I), wherein (I) and (II) have the structures shown below:

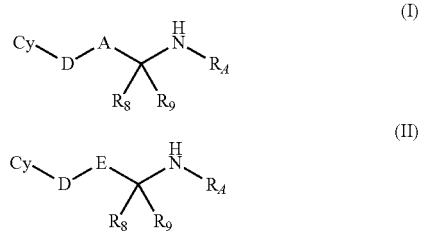

wherein:
$R_A$ is —$SO_2R_{10}$ or —$R_N$,
Cy is optionally substituted cyclohexadienyl;
D is an optionally substituted straight- or branched-chain $C_{1-4}$ alkyl group, or D is a group:

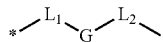

wherein:
$L_1$ is a covalent bond or optionally substituted $C_{1-3}$ alkyl;
$L_2$ is a covalent bond or optionally substituted $C_{1-2}$ alkyl; and
G is —O—, —S—, optionally substituted $C_{6-10}$ aryl, optionally substituted $C_{3-10}$ heteroaryl, or optionally substituted $C_{6-10}$ cycloalkyl;
and the asterisk indicates the point of attachment to Cy;
A is *—$CH_2NHC(R_6R_7)$— or *—$C(R_4R_5)NHCH_2$—, where the asterisk indicates the point of attachment to D;
E is *—$C(O)NHC(R_6R_7)$— or *—$C(R_4R_5)NHC(O)$—, where the asterisk indicates the point of attachment to D;
$R_4$ and $R_5$ are independently hydrogen, straight- or branched-chain $C_{1-20}$ alkyl, straight, branched or cyclic $C_{1-10}$ alkoxy, $C_{6-10}$ aryl, $C_{6-10}$ aryloxy, —OH, —CN, or —$CF_3$;

$R_6$, $R_7$, $R_8$ and $R_9$ are independently hydrogen, optionally substituted straight, branched or cyclic $C_{1-20}$ alkyl, optionally substituted straight, branched or cyclic $C_{1-20}$ alkoxy, optionally substituted $C_{6-20}$ aryl or optionally substituted $C_{6-20}$ aryloxy, or
$R_6$ and $R_7$ together with the carbon atom to which they are bound and/or $R_8$ and $R_9$ together with the carbon atom to which they are bound form an optionally substituted $C_{3-20}$ cycloalkyl or an optionally substituted $C_{2-20}$ cycloalkoxy, or
one of $R_6$ and $R_7$ and one of $R_8$ and $R_9$ together form an optionally substituted $C_{5-10}$ cycloalkyl or an optionally substituted $C_{5-10}$ cycloalkoxy;
$R_{10}$ is hydrogen, optionally substituted straight, branched or cyclic $C_{1-10}$ alkyl, optionally substituted $C_{6-10}$ aryl or —$NR_{11}R_{12}$, where $R_{11}$ and $R_{12}$ are, independently, optionally substituted straight- or branched-chain $C_{1-10}$ alkyl or optionally substituted $C_{6-10}$ aryl;
$R_N$ is hydrogen, or straight, branched or cyclic $C_{1-10}$ alkyl;
$R_{11}$ and $R_{12}$ are independently hydrogen, optionally substituted straight, branched or cyclic $C_{1-10}$ alkyl, or optionally substituted $C_{6-10}$ aryl, or
$R_{11}$ and $R_{12}$ together with the nitrogen atom to which they are bound form an optionally substituted $C_{2-10}$ cycloalkyl-amino group.

2. The method of claim 1, wherein Cy is a substituted cyclohexadienyl group.

3. The method of claim 2, wherein the cyclohexadienyl group is cyclohexa-1,4-dienyl.

4. The method of claim 1, wherein the cyclohexadienyl group is unsubstituted.

5. The method of claim 1, wherein $R_A$ is —$SO_2R_{10}$.

6. The method of claim 5, wherein $R_{10}$ is —$NMe_2$, pentafluorophenyl, methyl, 4-methyl-phenyl, 2,4,6-trimethylphenyl, or 2,4,6-triisopropylphenyl.

7. The method of claim 1, wherein $R_A$ is $R_N$.

8. The method of claim 7, wherein $R_N$ is hydrogen.

9. The method of claim 1, wherein D is substituted straight- or branched-chain $C_{1-4}$ alkyl.

10. The method of claim 9, wherein D is —$(CH_2)_2$— or —$(CH_2)_3$—.

11. The method of claim 1, wherein A is *—$C(R_4R_5)$ $NHCH_2$— and E is *—$C(R_4R_5)NHC(O)$—.

12. The method of claim 11, wherein $R_4$ and $R_5$ are each hydrogen.

13. The method of claim 1, wherein A is *—$CH_2NHC$ $(R_6R_7)$— and E is *—$C(O)NHC(R_6R_7)$—.

14. The method of claim 13, wherein $R_6$ and $R_7$ are each hydrogen.

15. The method of claim 1, wherein $R_6$, $R_7$, $R_8$ and $R_9$ are, independently, hydrogen or optionally substituted $C_{6-10}$ aryl.

16. The method of claim 15, wherein $R_6$, $R_7$, $R_8$ and $R_9$ are independently hydrogen or optionally substituted phenyl.

17. The method of claim 1, wherein the reduction of the amide of formula (II) to form the amine compound of formula (I) is accomplished using a metal hydride reducing agent or hydrogen in the presence of a hydrogenation catalyst.

18. The method of claim 1, wherein the reducing agent is $LiAlH_4$, $LiAlH(OMe)_3$, $LiAlH(OEt)_3$, or $AlH_3$.

* * * * *